(12) United States Patent
Han et al.

(10) Patent No.: US 8,975,241 B2
(45) Date of Patent: Mar. 10, 2015

(54) COMPOSITION FOR TREATING AND PREVENTING OBESITY INCLUDING HIGH WATER-SOLUBLE 2-HYDROXYPROPYL-BETACYCLODEXTRIN AS EFFECTIVE COMPONENT

(75) Inventors: Gyoon-Hee Han, Hwaseong (KR); Yong Seok Choi, Seoul (KR); Sang-Bae Han, Cheongju (KR); Jong-Ho Lee, Gunpo (KR); Hwan-Mook Kim, Daejeon (KR); Song-Kyu Park, Daejeon (KR); Ki-Ho Lee, Seoul (KR); Jong-Soon Kang, Chungcheongbuk-do (KR); Ki-Hoon Lee, Daejeon (KR); Chang-Woo Lee, Chungcheongbuk-do (KR)

(73) Assignee: Song Ho Biomed Co., Ltd., Gunpo-Si (KR)

( * ) Notice: Subject to any disclaimer, the term of this patent is extended or adjusted under 35 U.S.C. 154(b) by 238 days.

(21) Appl. No.: 13/500,843

(22) PCT Filed: Oct. 8, 2010

(86) PCT No.: PCT/KR2010/006912
§ 371 (c)(1),
(2), (4) Date: Apr. 6, 2012

(87) PCT Pub. No.: WO2011/043630
PCT Pub. Date: Apr. 14, 2011

(65) Prior Publication Data
US 2012/0196831 A1    Aug. 2, 2012

(30) Foreign Application Priority Data

| Oct. 8, 2009 | (KR) | 10-2009-0095568 |
| Oct. 8, 2009 | (KR) | 10-2009-0095569 |
| Nov. 3, 2009 | (KR) | 10-2009-0105449 |

(51) Int. Cl.
| A61K 31/724 | (2006.01) |
| A23L 1/09 | (2006.01) |
| A23L 1/30 | (2006.01) |

(52) U.S. Cl.
CPC ........... *A61K 31/724* (2013.01); *A23V 2002/00* (2013.01); *A23L 1/095* (2013.01); *A23L 1/30* (2013.01)

USPC .............................................. 514/58

(58) Field of Classification Search
None
See application file for complete search history.

(56) References Cited

U.S. PATENT DOCUMENTS

| 6,855,358 B1 * | 2/2005 | Nickolas et al. .............. 426/335 |
| 2003/0130231 A1 | 7/2003 | Regiert et al. |
| 2005/0051483 A1 * | 3/2005 | Majeed et al. ................ 210/634 |

FOREIGN PATENT DOCUMENTS

| JP | 06-080706 | 3/1994 |
| JP | 11-506922 | 6/1999 |
| JP | 2006-191830 | 7/2006 |
| JP | 2007-505040 | 3/2007 |
| JP | 2009-520693 | 5/2009 |
| JP | 2009-137916 | 6/2009 |
| KR | 10-2004-0012696 | 2/2004 |

OTHER PUBLICATIONS

Haynes, A. et al "Anorectic, thermogenic and anti-obesity activity . . . " Regulatory Peptides (2002) vol. 104, pp. 153-159.*
Valentino J. Stella et.al., "Cyclodextrins," Toxicologic Pathology, vol. 36 No. 1 p. 30-42, Jan. 2008.

* cited by examiner

*Primary Examiner* — Leigh Maier
(74) *Attorney, Agent, or Firm* — Lexyoume IP Meister, PLLC

(57) ABSTRACT

There is provided a composition for preventing and treating obesity including high water-soluble β-cyclodextrin derivatives as an effective component. Specifically, the composition including the high water-soluble β-cyclodextrin derivatives, especially, 2-hydroxypropyl-β-cyclodextrin (HP-β-CD, HPBCD) has effects on suppressing an increase in body weight induced by a high fat diet, suppressing appetite through decreasing an amount of dietary intake, decreasing body fat, decreasing liver weight, and significantly decreasing a sharp increase of blood sugar induced by intaking glucose and maltose on an empty stomach so that it can be useful for preventing and treating obesity, preventing and treating various diseases induced by obesity, and suppressing a sharp increase of blood sugar after dinner.

2 Claims, 18 Drawing Sheets

COMPOSITION FOR TREATING AND PREVENTING OBESITY INCLUDING HIGH WATER-SOLUBLE 2-HYDROXYPROPYL-BETACYCLODEXTRIN AS EFFECTIVE COMPONENT

BACKGROUND OF THE INVENTION

1. Field of the Invention

The present invention relates to a composition for treating and preventing obesity, a composition for suppressing appetite, or a composition for lowering blood sugar, including high water-soluble β-cyclodextrin derivatives, especially, 2-hydroxypropyl-β-cyclodextrin as an effective component.

2. Description of the Related Art

Obesity is one of the most common nutrition disorders around the world and refers to the accumulation of extra calorie in a form of fat in the body through intaking excessive calorie as compared with calorie to be burnt. According to WHO statistical data, the number of overweight people is now approximately 250 million and it is expected to be approximately 300 million who are suffered from obesity after 20 years. Approximately 50% of American adults are suffered from obesity or overweight, i.e., BMI≥25, and it is reported that one of four adults has above 25 of BMI, which means obese, according to the recent domestic statistical data (Ministry of Health and Welfare., Report on 1998 National health and nutrition survey, 2000; Lee B G., et al., *J. Kor. Soc. Study Obesity*, 11(2), pp 131-140, 2002).

It is generally understood that obesity is caused by various causes, such as a hereditary effect, environmental influences caused by a westernized dietary life, a psychological effect caused by stress, etc., but the accurate cause or mechanism is not precisely established so far. However, there is a lot of interest in an obesity treatment around the world because obesity can cause other diseases, such as cardiovascular disease or diabetes as well as the problems of obesity itself (Manson, et al., *New England J. Med.*, 333, pp 677-685, 1995; Kopleman P G., *Nature*, 404, pp 635-643, 2000; Must, et al., *JAMA*, 282, pp 1523-1529, 1999).

In addition, obesity is strongly related to the causes for all sorts of adult diseases, as well as an external problem so that higher the degree of obesity is increased, higher the prevalence rates of diabetes, cholelithiasis, hypertension, a cardiac disorder, a stroke, etc., are increased (Field A E., et al., *Arch. Intern, Med.*, 161(13), pp 1581-1586, 2001; Cha B R., et al., *Kor. J. Nutr.*, 36(5), pp 483-490, 2003). Accordingly, the financial burden and a loss of lives caused by obesity are enormous. The results of the epidemiological survey that was performed in America suggest that the death from the disease related to obesity reached 28,000 in 1991; approximately 80% of them had morbid obesity, i.e., BMI≥30; and approximately 120 trillion won were spent for treating the obesity-related diseases in a year.

It is reported that with the growing interest in the regulation of body weight as mentioned above, 48.1% of women in their 20's and 40% of women in their 30's had the experience in the regulation of body weight during the passing year (Kae S H., Patterns of body weight and diet for Korean-1998 National health and nutrition survey—Proceeding for Korean Community Nutrition., Society spring Conference, 7-28, 2001). Our domestic weight loss market was growing rapidly to be estimated to be 2000 hundred million in 2001 and 3000 hundred million in 2002. It has already been announced that weight-control foods, in which its imports are approved in a normal price, increased by a surprising 110 times in recent 2 years. However, the above products are becoming a problem in the aspect of effectiveness and many examples about side effects in use have been reported (Lee B G., et al., *J. Kor. Soc. Study Obesity*, 11(2), pp 131-140, 2002; *Food and environment*, 2002. 9. 18).

Meanwhile, many types of methods and results for treating obesity are presented and living habits have to be reformed basically in order to treat obesity and maintain proper weight because the obesity causes the accumulation of extra energy in the body by intaking excessive energy or reducing energy consumption (Lee B G., et al., *J. Kor. Soc. Study Obesity*, 11(2), pp 131-140, 2002; Wadden T A., et al., *arch. of Intern. Med.*, 161, pp 218-27, 2001). There are theoretical grounds for preventing the decreases of a basal metabolic rate and fat free mass by intaking calorie with more than basal metabolic rate as a low calorie dietary cure in the process of reforming living habits (Kang J H., et al., *J. Kor. Acad. Fam. Med.*, 19 (2), pp 167-176, 1998).

Meanwhile, another important therapy in addition to a dietary therapy is an exercise cure. It is an established fact that regular exercise is good for the regulation of body weight, but the researches as to whether using a combination of the low calorie dietary cure and regular exercise would be advantageous or not has shown conflicting results according to the researches (Moyer C L., et al., *Am. J. clin. Nutr.*, 50, pp 1324-327, 1989; Donnelly J E., et al., *Am. J. clin. Nutr.*, 54, pp 56-61, 1991).

In addition, a study on body modulating function of various foods is being intensively performed, and also in the field of obesity, the study is proceeding to reduce body weight by using various food materials, such as red ginseng, aloe, hydroxycitrate (HCA), flavonoid, carnitine, chitosan, capsaicin, etc. (Oh S J., et al., *J. Kor. Soc. Study Obesity*, 9, pp 209-218, 2000; Lee H Y., *J. Kor. Soc. Study Obesity*, 6, pp 75-84, 1997; Moon S J., et al., *Korean J. Nutrition*, 30, pp 155-169, 1997).

Despite the developments of the above-mentioned various obesity medicines, there are frequent occasions that fall short of our expectations about the activity of those obesity medicines for suppressing obesity and also induce various side effects, such as dizzy, thirst, vomit, etc., when administering continuously so that there is a still requirement for an effective treatment of obesity.

Diabetes mellitus (DM) is mostly a complex chronic disorder of carbohydrate, fat, and protein metabolisms generated from a lack of cell insulin receptor or a partially or completely lack of insulin secretion by β cells of a pancreas. In the case of an average man, insulin and glucagon are generated in vivo to reduce or increase blood sugar complementarily so that it can maintain a proper concentration of blood sugar in vivo. Insulin is produced, then stored in β cells, and then secreted into blood when increasing blood sugar. The secreted insulin is bonded to an insulin receptor on the surface of muscle cells or hepatic cells to introduce in cells and then D-glucose is introduced from blood into the body to operate a sugar metabolism process.

Only approximately 0.5% of the entire population suffered from diabetes before 1970 in our country so that the medical community had little interest about diabetes, but the rate of patients suffered from diabetes has been estimated to be 2%~3% in 1980 and 4%~6% (approximately 1.5~2 million people) in 1990, and also there are significant numbers of people who did not recognize the fact that they had diabetes.

A symptom of diabetes is very diverse, but polyuria, polydipsia, polyphagia, etc are the most dominant. A patient suffered from diabetes does not use glucose as an energy source so that protein and fat that are already stored are consumed and then a vicious cycle of such phenomenon leads to weight lose.

Diabetes is largely divided into an insulin-dependent diabetes (Type I diabetes) and an insulin-independent diabetes (Type II diabetes). Type I diabetes is in a state of merely secreting insulin through a decrease of pancreatic β cell function due to a genetic cause, a viral infection, etc. Type I diabetes is mainly developed in 10's~20's by sudden and is known as a juvenile-onset, a brittle, or a ketosis diabetes. The causes of Type II diabetes are unknown, but are well occurred after 40's due to a family history of diabetes, obesity, stress, etc. It is known that for Type II diabetes, insulin is sufficiently secreted in a pancreas but an insulin resistance and glucose uptake are different from the normal so that even though it is hyperinsulinemia, blood sugar does not be normal and there is maturity-onset diabetes, adult-onset diabetes, ketosis-resistant diabetes, or stability diabetes.

Diabetes itself is not a serious disease, but when its treatment is delayed to be chronic, complications, for example diabetic retinopathy (causes of visual impairment, blindness, retinal hemorrhage, retinopathy, and cataracts), diabetic nephropathy, Diabetic Peripheral Neuropathy, cardiac and the circulating system disorders (cause of angiopathy), periodontitis, osteopenia, skin diseases, etc, are problems. The pathologic complications of the diabetes are known to be basically proportional to hyperglycemia (Porte, Jr. et. al., 1996).

Recently, the most commonly used medicine for treating diabetes is largely divided into oral hypoglycemic agents and insulin injections. Generally, it has been the commonly accepted view that insulin should be injected to a patient with insulin-dependent diabetes who cannot secrete insulin in vivo and a patient with insulin-independent diabetes who suffers from gestational diabetes and cannot control blood sugar by using oral hypoglycemic agents, and the oral hypoglycemic agents should be taken by a patient suffered from insulin-independent diabetes who cannot properly control blood sugar even though the patient is combining both exercise and diet.

The insulin injections are intravenously or intramuscular administered, but mostly subcutaneously administered in the case of a long period of administration. However, in the case of a subcutaneously injection, there is a problem that an insulin effect is decreased because insulin is not sharply increased, when taking in foods, a secretion of insulin is decreased, and it is a liver circulation rather than a peripheral circulation (Goodman, et. al., *The Pharmacological basis of Therapeutics*, p 1692).

The oral hypoglycemic agents that are generally used may be classified into a sulfonylurea-based drug, a biguanide-based drug, α-glucosidase inhibitor, etc (Deruiter, Endocrine Pharmacology Module, Spring, 2003). Example of the sulfonylurea-based drug includes glipizide, glyclazide, gliquidone, glibenclamide, chlorpropamide, etc, and acts as an accelerator of insulin secretion in a pancreas. Accordingly, they cannot be used for a patient with insulin-dependent diabetes who can never secrete insulin in a pancreas, but they can be used for a patient with insulin-independent diabetes who has a relatively reduced ability for secreting insulin in a pancreas but there is a disadvantage that women of childbearing age cannot use because it can lead to fetal deformities (fetal macrosomia), miscarriage, a stillbirth, etc. In addition, when overdoses of the drugs are administered or administered on an empty stomach, these drugs may cause hypoglycemia and also cause side effects, such as skin rashes, jaundice, loss of appetite, nausea (queasiness), diarrhea, etc. The biguanide-based drug is metformin, etc, has a lower hypoglycemic effect than that of the sulformylurea-based drug, but has low possibility for causing hypoglycemia. However, it is now in use only for an experimental drug in the United States because the side effect rate in a digestive system is high so that nausea, queasiness, diarrhea, rashes, etc are caused at the very beginning of treatment and lactic acidosis is induced to cause a fatal side effect and then threaten one's life.

As mentioned above, a recent method for controlling diabetes is limited only to a few methods and their approaches are different from a natural glycometabolism control of the human body so that it affects negatively the human body thereby requiring the development of the drug for substituting existing insulin and oral hypoglycemic agent.

Cyclodextrin is a ring-shaped oligosaccharide with 6~12 glucose molecules bonded together in an α-1,4-glycoside bond, and includes alpha(α)-cyclodextrin having 6 glucose molecules bonded, beta (β)-cyclodextrin having 7 glucose molecules bonded, gamma(γ)-cyclodextrin having 8 glucose molecules bonded, delta(δ)-cyclodextrin having 9 glucose molecules bonded, epsilon(ε)-cyclodextrin having 10 glucose molecules bonded, and zeta(ζ)cyclodextrin having 11 glucose molecules bonded. Above this, cyclodextrins having at least 12 glucose molecules are being developed.

The cyclodesxtrin has a three dimensional structure consisting of a hydrophobic inside and a hydrophillic outside so that it is soluble in water and also has a function for including various fat-soluble materials. The above-mentioned function of cyclodextrin can increase solubility of non-soluble materials and also the cyclodextrin can facilitate coverings of taste and smell, stabilization of a deliquescent substance, a decrease of stimulus, etc so that it is being used for a medical industry, a food industry, etc, variously.

Until now, the cyclodextrin may be used for a long life preservation and powderization of toxic volatility, an odorless of bad smell substance, a prevention of flavoring volatilization, a preservation of a flavoring, and a substrate of a powder flavoring; as a drug delivery system including insulin because it includes an effective component of drug, a flavoring and a smell inside of pores, and releases slowly; as a retardative agent or an accelerator of inclusion reaction because it can mix with a unstable material by an inclusion and react with other materials in a state of protecting a part of functional group; as an emulsifier or surfactant because it has an emulsifying function to a non-soluble material; as a stabilizer to an easily oxidizable material or an UV-unstable compound because it prevents an oxidation or photolysis; for removing toxic substances from domestic waste water because it can include harmful heavy metals; as a stabilizer for a long-life quality as a substance for foods or drinks; for preparing packaging products, a fiber, and agricultural products because it can include antimicrobials; as a gel and thickener; and as alternate products for an oil and dietary fibers (Bun-Sam, Lim, a research paper, Korea Institute of Science and Technology Information (KISTI), a ring-shaped multifunctional material cyclodextrin, 2003).

Meanwhile, α-cyclodextrin is commercially available as a diet supplement for losing weight named with FBCx in the United States. When FBCx (10% of the total amount of fat) is added in high-fat feeds including 40% of soybean oil and the feeds are provided to rat for 6 weeks, the rat's weight is reduced by 7.4% as compared with the group of high-fat feeds without FBCx (Artiss J D., et al., *Metab. Clin. Exp.*, 55, pp 195-202, 2006). For a clinical test about obesity with Type II diabetes for 3 months, while the weights of the patients who taken in only diet containing fat are increased, the weights of the patients who taken in the diet containing fat along with FBCx are not decreased but not increased (Grunberger G., et al., *Diabetes Metab. Res. Rev.* 23, pp 56-62, 2007).

It is known that the α-cyclodextrin has 57 nm of diameter of inside cavity, but β-cyclodextrin further including one molecule of glucose as compared with the α-cyclodextrine has 78 nm of diameter of inside cavity thereby including larger molecule than the α-cyclodextrin so that the interaction with wider variety of molecules can be expected (Brewster M E and Loftsson T., *Adv. DrugDeliv. Rev.* 59, pp 645-666, 2007). Study on bonding ability of the α-cyclodextrin with fat indicated that the α-cyclodextrin and fat were bonded in the rate of 1:9 confirmed by measuring a level of emulsion formed by the α-cyclodextrin (Grunberger G., et al., *Diabetes Metab. Res. Rev.* 23, pp 56-62, 2007).

Meanwhile, the experiment for measuring an antiobesity effect using mouse and human indicated that the β-cyclodextrin acts to suppress a weight increase and reduce weight, respectively (Kim D W., et al., *Food Sci. Biotechnol.*, 17, pp 700-704, 2008, Park B S., *J. Korean Soc. Food Sci. Nutr.* 33, pp 832-838, 2004). However, it is known that the β-cyclodextrin has a relatively low solubility in water (18.5 mg/ml at 25° C.) so that it is difficult to prepare water-soluble formulation with high concentration.

2-hydroxypropyl-β-cyclodextrin is a derivative produced by a reaction between β-cyclodextrin and propylene oxide; and has a higher water-solubility than that of cyclodextrin and is harmless to humans so that it is frequently used as an alternate product for cyclodextrin in a medical and food industry, etc.

Specifically, as the report about a use of 2-hydroxypropyl-β-cyclodextrin, Korean Publication No. 10-1995-0018059 discloses that it was used as absorption and biological agent for increasing utility rate through a rectum mucous membrane of omeprazole; Korean Patent No. 10-0473716 discloses that hydroxypropyl-β-cyclodextrin was used as skin preparation for external use for treating an atopic dermatitis and psoriasis; Korean Publication No. 10-2009-0084925 discloses that it was used as a drug for treating or preventing a congestive heart failure; Korean Publication No. 10-2009-0010953 discloses that it was used as anesthesia, anti-inflammation or anti-pyrogenic drug; Korean Patent No. 10-0441121 discloses that it was used as a composition for a skin care; and Korean Publication No. 10-2008-0046164 discloses that it was used as a drug for reducing a toxic effect of ionizing radiation.

However, there is no report that hydroxypropyl-β-cyclodextrin has an effect on suppressing appetite and reducing weight and body fat. In addition, there is no report that hydroxypropyl-β-cyclodextrin has a hypoglycemic effect after dinner or can be used for treating diabetes.

Accordingly, the present inventors tried to develop antiobesity drug that is more efficient. As a result of testing the identified stable derivative of β-cyclodextrin, it was confirmed that high water-soluble β-cyclodextrin derivatives, especially, 2-hydroxypropyl-β-cyclodextrin has effects on suppressing a increase in body weight induced by a high fat diet, suppressing appetite through a decrease of dietary intake, decreasing body fat, preventing and treating obesity by reducing liver weight, and preventing and treating various diseases caused by obesity thereby completing the present invention.

In addition, the present inventors tried to develop a new hypoglycermic drug. Consequently, it was confirmed that high water-soluble β-cyclodextrin derivatives, especially, hydroxypropyl-β-cyclodextrin (HPBCD) has an effect on suppressing a sharp increase of blood sugar induced by intaking glucose and maltose on an empty stomach in a normal mouse (ICR) and it can be very useful as an effective component of a pharmaceutically composition for decreasing blood sugar after dinner so that the present invention was completed.

SUMMARY OF THE INVENTION

Object of the present invention is to provide a composition for preventing and treating obesity, including high water-soluble β-cyclodextrin derivatives as an effective component.

Another object of the present invention is to provide a composition for suppressing appetite, including high water-soluble β-cyclodextrin derivatives as an effective component.

Still another object of the present invention is to provide a composition for preventing and treating diseases caused by obesity, including high water-soluble β-cyclodextrin derivatives as an effective component.

Still another object of the present invention is to provide a composition for lowering blood sugar, including high water-soluble β-cyclodextrin derivatives as an effective component.

In order to achieve the above objects, the present invention provides a pharmaceutical composition for preventing and treating obesity, including high water-soluble β-cyclodextrin derivatives as an effective component.

In addition, the present invention provides a pharmaceutical composition for suppressing appetite, including high water-soluble β-cyclodextrin derivatives as an effective component.

In addition, the present invention provides a pharmaceutical composition for preventing and treating diseases caused by obesity, including high water-soluble β-cyclodextrin derivatives as an effective component.

In addition, the present invention provides a pharmaceutical composition for suppressing an increase in body weight, including high water-soluble β-cyclodextrin derivatives as an effective component.

In addition, the present invention provides a pharmaceutical composition for decreasing body fat, including high water-soluble β-cyclodextrin derivatives as an effective component.

In addition, the present invention provides health functional foods for preventing and improving obesity, including high water-soluble β-cyclodextrin derivatives as an effective component.

In addition, the present invention provides health functional foods for suppressing appetite, including high water-soluble β-cyclodextrin derivatives as an effective component.

In addition, the present invention provides health functional foods for preventing and improving diseases caused by obesity, including high water-soluble β-cyclodextrin derivatives as an effective component.

In addition, the present invention provides health functional foods for suppressing an increase in body weight, including high water-soluble β-cyclodextrin derivatives as an effective component.

In addition, the present invention provides health functional foods for decreasing body fat, including high water-soluble β-cyclodextrin derivatives as an effective component.

In addition, the present invention provides a method for preventing or treating obesity, including administering an effective amount of high water-soluble β-cyclodextrin derivatives to an object.

In addition, the present invention provides a method for suppressing appetite of an object, including administering an effective amount of high water-soluble β-cyclodextrin derivatives to the object.

In addition, the present invention provides a method for preventing or treating diseases caused by obesity, including administering an effective amount of high water-soluble β-cyclodextrin derivatives to an object.

In addition, the present invention provides a method for decreasing body fat of an object, including administering an effective amount of high water-soluble β-cyclodextrin derivatives to the object.

In addition, the present invention provides a use of high water-soluble β-cyclodextrin derivatives for preparing a composition for preventing or treating obesity.

In addition, the present invention provides a use of high water-soluble β-cyclodextrin derivatives for preparing a composition for suppressing appetite.

In addition, the present invention provides a use of high water-soluble β-cyclodextrin derivatives for preparing a composition for preventing or treating diseases caused by obesity.

In addition, the present invention provides a use of high water-soluble β-cyclodextrin derivatives for preparing a composition for decreasing body fat.

In addition, the present invention provides a composition for lowering blood sugar, including high water-soluble β-cyclodextrin derivatives as an effective component.

In addition, the present invention provides a composition for suppressing glycolysis in the gastrointestinal tract, including high water-soluble β-cyclodextrin derivatives as an effective component.

In addition, the present invention provides a composition for suppressing absorption of sugar in the gastrointestinal tract, including high water-soluble β-cyclodextrin derivatives as an effective component.

In addition, the present invention provides health functional foods for lowering blood sugar, including high water-soluble β-cyclodextrin derivatives as an effective component.

In addition, the present invention provides a method for lowering blood sugar of an object, including administering an effective amount of high water-soluble β-cyclodextrin derivatives to the object.

In addition, the present invention provides a method for suppressing glycolysis in the gastrointestinal tract of an object, including administering an effective amount of high water-soluble β-cyclodextrin derivatives to the object.

In addition, the present invention provides a method for suppressing absorption of sugar in the gastrointestinal tract of an object, including administering an effective amount of high water-soluble β-cyclodextrin derivatives to the object.

In addition, the present invention provides a use of high water-soluble β-cyclodextrin derivatives for preparing a composition for lowering blood sugar.

In addition, the present invention provides a use of high water-soluble β-cyclodextrin derivatives for preparing a composition for suppressing glycolysis in the gastrointestinal tract.

In addition, the present invention provides a use of high water-soluble β-cyclodextrin derivatives for preparing a composition for suppressing absorption of sugar in the gastrointestinal tract.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Figure 1:
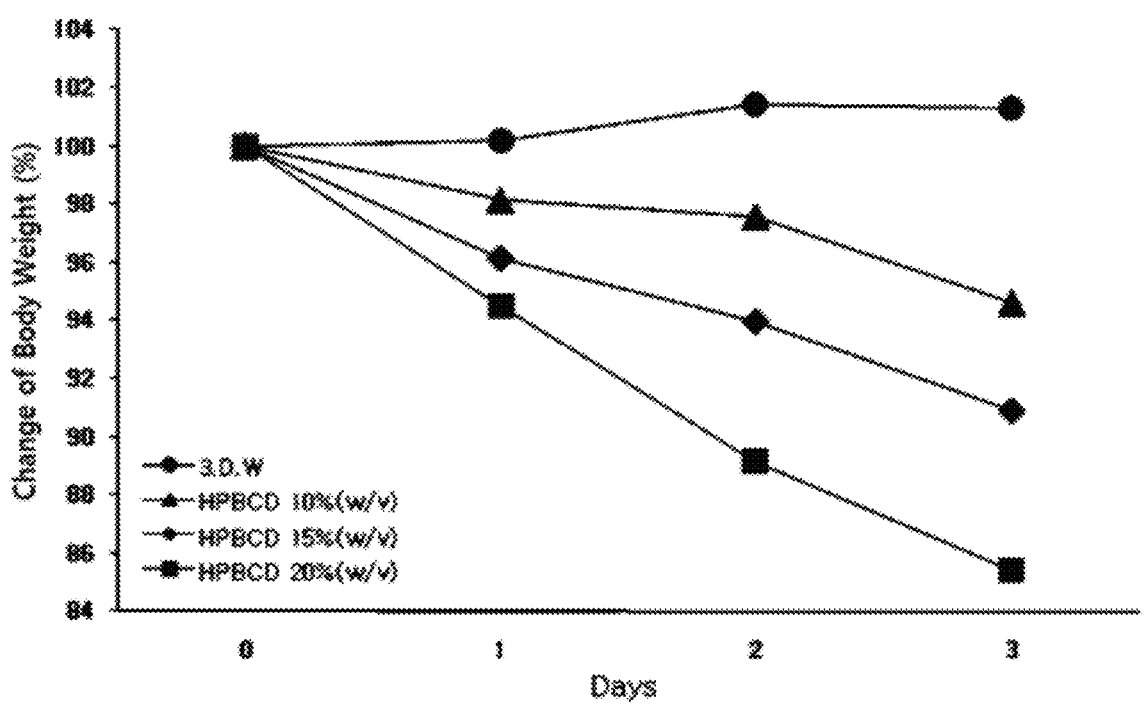
FIG. 1 is a graph showing an effect on decreasing body weight for autonomically drinking a drinking water including 10%, 15%, and 20% (W/V) of 2-hydroxypropyl-β-cyclodextrin (2-HPBCD) in a mouse model with obesity caused by a high fat diet.

Exemplary embodiments of the present invention will now be described in detail with reference to the accompanying drawings.

β-cyclodextrin derivatives according to the present invention has a structure of the following Chemical Formula 1:

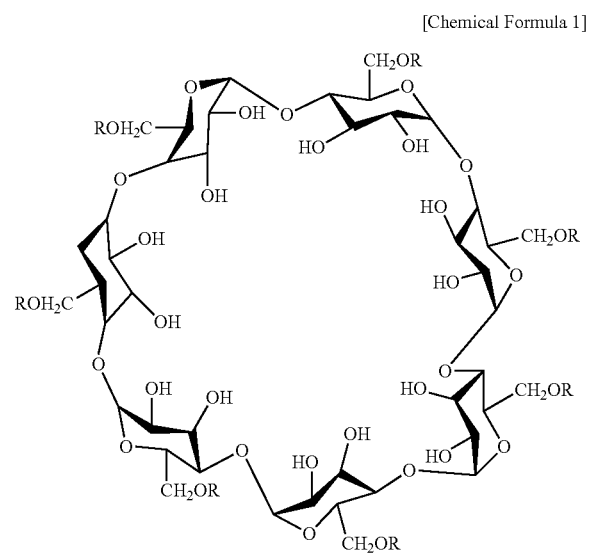

[Chemical Formula 1]

(where,

R is $C_1$-$C_4$ linear or branched alkyl, $C_1$-$C_4$ linear or branched hydroxy alkyl, or $C_1$-$C_4$ linear or branched sulfoalky; preferably methyl, hydroxypropyl, 2-hydroxypropyl, or sulfobuthyl; and more preferably 2-hydroxypropyl.)

For the present invention, β-cyclodextrin derivatives may be prepared by introducing a new functional group or modifying a part of its molecular structure from β-cyclodextrin as disclosed in the above reference documents. At this point, the β-cyclodextrin may be prepared by using various preparing method, such as an organic solvent method, a non-organic solvent method, an enzyme processing, or a continuous producing process using a bioreactor. The above preparing methods are detailedly disclosed in the reference document (Bun-Sam, Lim, a research paper, Korea Institute of Science and Technology Information (KISTI), a ring-shaped multifunctional material cyclodextrin, August, 2003).

For the present invention, 2-hydroxypropyl-β-cyclodextrin may be commercially available in the market or may be prepared by a synthesis using β-cyclodextrin and propylene oxide as disclosed in the known preparing method (WO/1990/012035).

For the present invention, hydroxypropyl cyclodextrin with 2-hydroxypropyl as R has a type of a white powder and chemicophysical properties, such as 1380~1480 Da of molecular weight, 65 g/mL at 25° C. and 80 g/mL at 50° C. of water-solubility, approximately 300° C. of decomposition temperature, approximately 5% of moisture content, 0.62 nm of inside diameter, and 52~69 mN/m of surface tension.

Since 2-hydroxypropyl-β-cyclodextrin has a sweet taste and high solubility so that it is easy to take by adding water and also to take a considerable amount, it may have a great curative power.

In addition, the 2-hydroxypropyl-β-cyclodextrin has proven effect as an excipient that has been announced by Food and Drugs Administration so that it is stable even if a massive overdose of itself is taken.

The present invention provides a pharmaceutical composition for preventing and treating obesity, including high water-soluble β-cyclodextrin derivatives as an effective component.

In addition, the present invention provides a pharmaceutical composition for preventing or treating diseases caused by obesity, including high water-soluble β-cyclodextrin derivatives as an effective component.

The diseases caused by obesity may be preferably any one selected from the group consisting of hypertension, hyperlipemia, arteriosclerosis, coronary disease, cerebropathia, and diabetes, but the present invention is not limited thereto.

In addition, the present invention provides a pharmaceutical composition for decreasing body fat, suppressing an increase in body weight, or suppressing appetite, including high water-soluble β-cyclodextrin derivatives as an effective component.

The high water-soluble β-cyclodextrin derivatives may be a type of salt.

In Example 1 of the present invention, in order to confirm an effect of high water-soluble β-cyclodextrin derivatives, a change in body weight and an amount of dietary intake were measured after autonomically drinking the 2-hydroxypropyl-β-cyclodextrins with various concentrations by using an animal model suffered from obesity caused by a high fat diet. As a result, the 2-hydroxypropyl-β-cyclodextrin decreased body weight depending on the concentrations as compared with the control group that was administered with sterile distilled water and had a significant effect on decreasing body weight as compared with initial body weight (see FIG. 1). In addition, it also had an effect on suppressing appetite decreasing an amount of feed intake (see FIG. 2).

Figure 3:
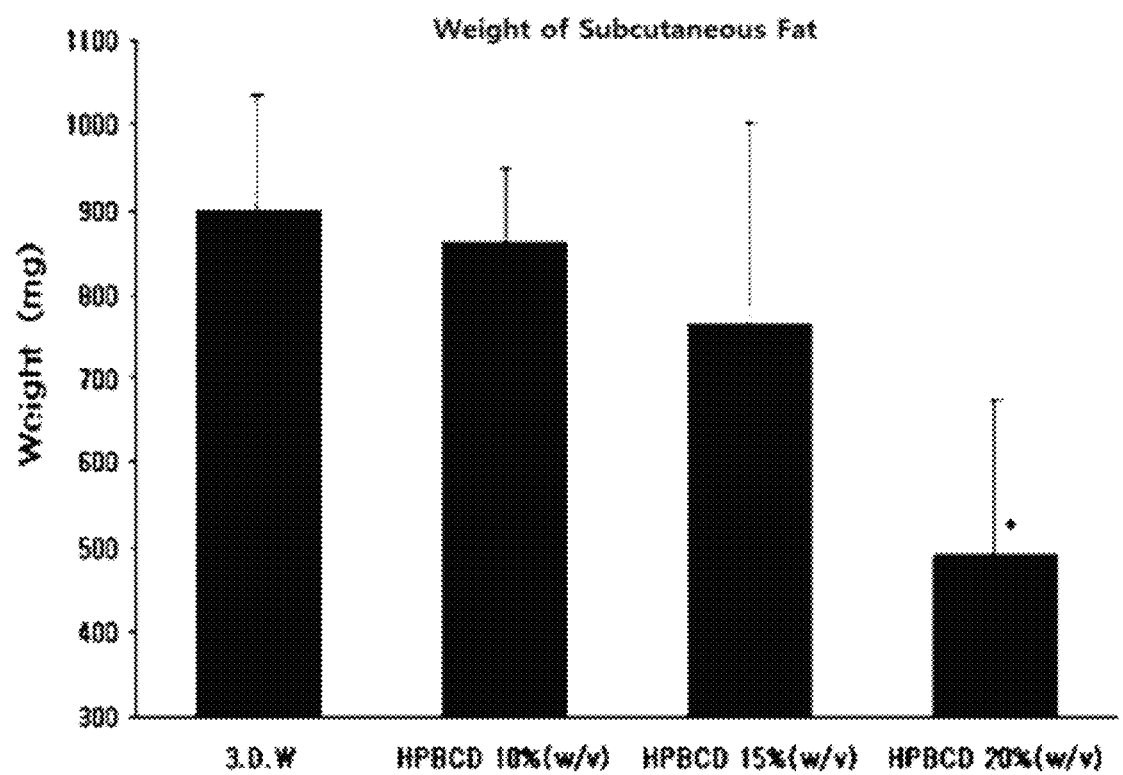
FIG. 3 is a graph showing a change of weight of subcutaneous fat for autonomically drinking a drinking water including 10%, 15%, and 20% (W/V) of 2-HPBCD in a mouse model with obesity caused by a high fat diet.
Figure 4:
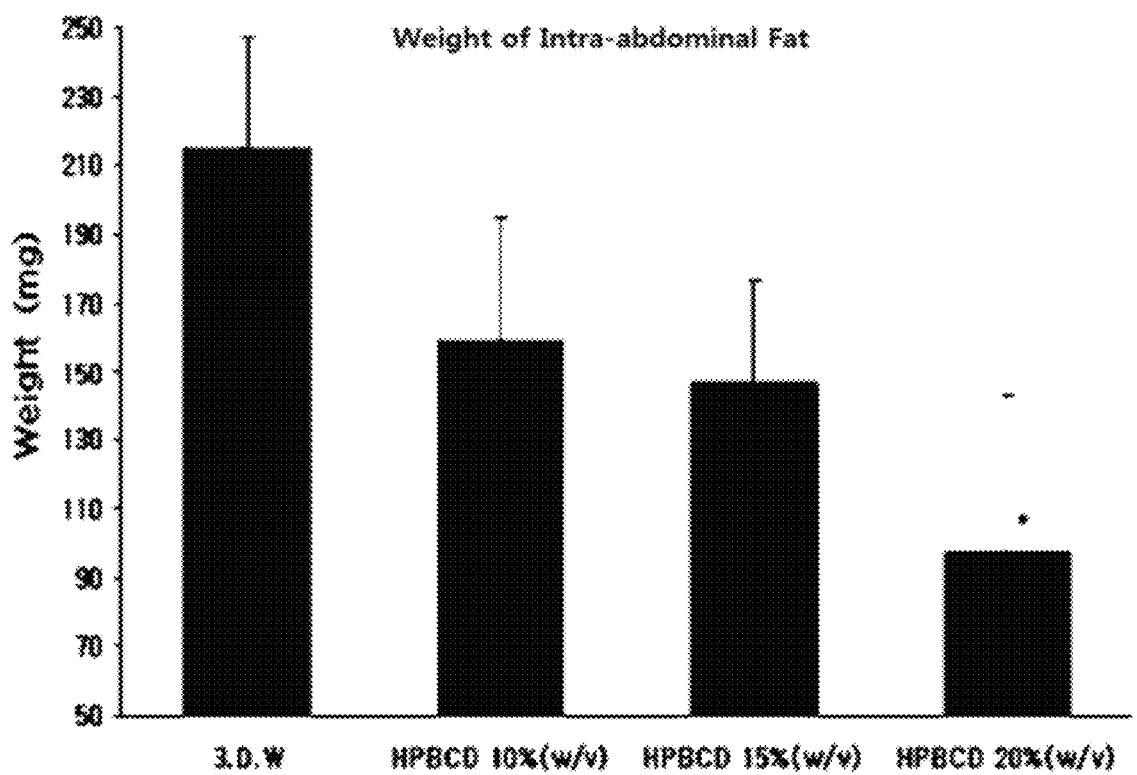
FIG. 4 is a graph showing a change of weight of genital fat for autonomically drinking a drinking water including 10%, 15%, and 20% (W/V) of 2-HPBCD in a mouse model with obesity caused by a high fat diet.
Figure 5:
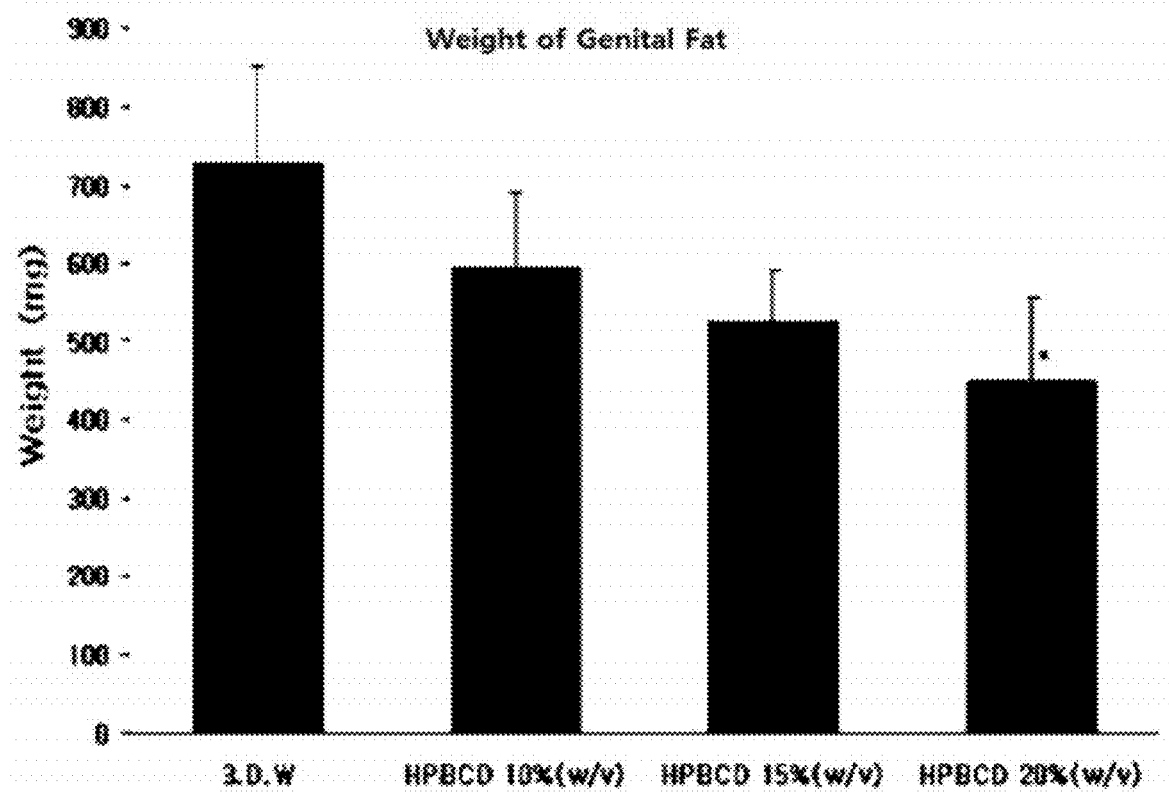
FIG. 5 is a graph showing a change of weight of intra-abdominal fat for autonomically drinking a drinking water including 10%, 15%, and 20% (W/V) of 2-HPBCD in a mouse model with obesity caused by a high fat diet.
Figure 6:
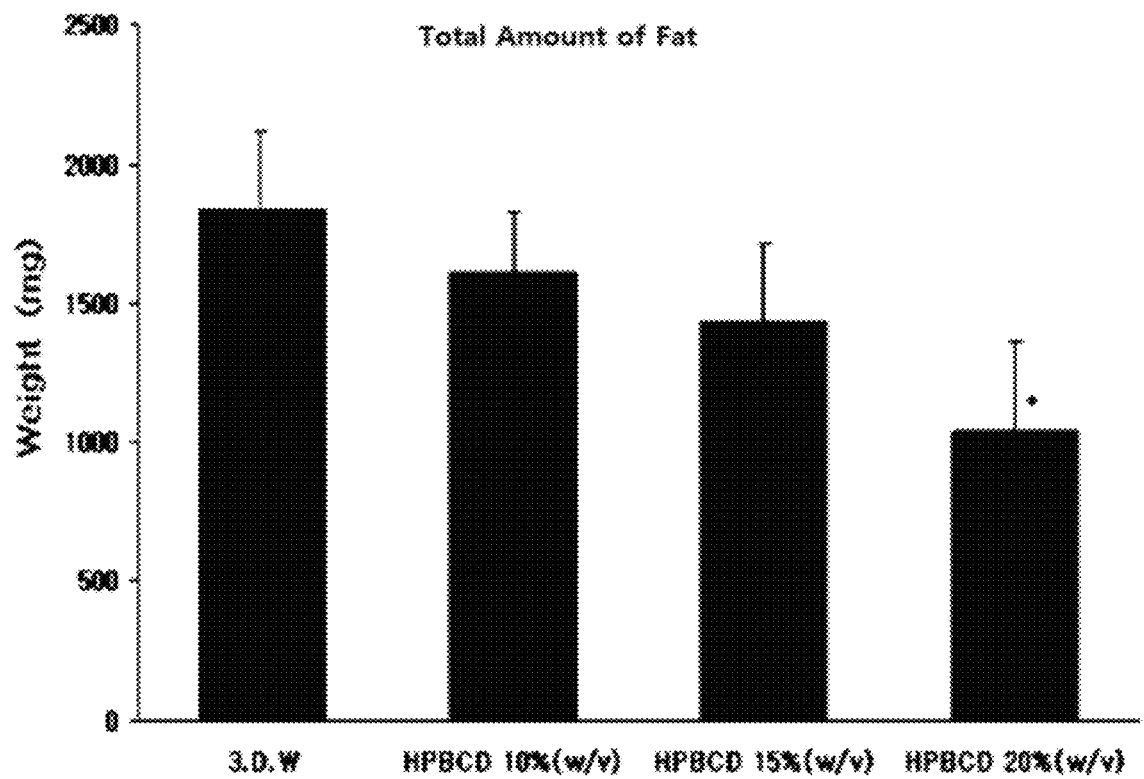
FIG. 6 is a graph showing a change of total weight of fat for autonomically drinking a drinking water including 10%, 15%, and 20% (W/V) of 2-HPBCD in a mouse model with obesity caused by a high fat diet.
Figure 7:
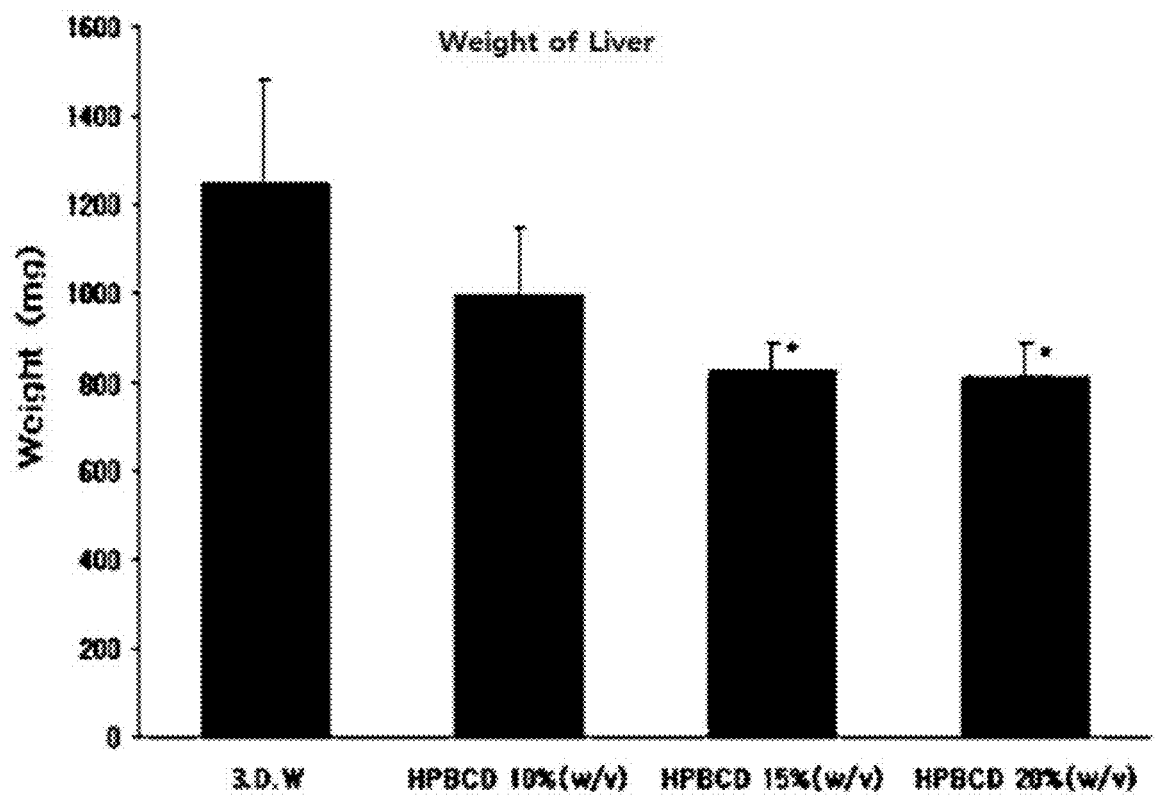
FIG. 7 is a graph showing a change of weight of liver for autonomically drinking a drinking water including 10%, 15%, and 20% (W/V) of 2-HPBCD in a mouse model with obesity caused by a high fat diet.

In Example 2 of the present invention, changes of the weights of subcutaneous fat, genital fat, and intra-abdominal fat, total amount of fat, and weight of liver were measured, respectively, by autopsying after autonomically drinking the 2-hydroxypropyl-β-cyclodextrins with various concentrations by using an animal model suffered from obesity caused by a high fat diet. As a result, the 2-hydroxypropyl-β-cyclodextrin had effects on decreasing the weights of subcutaneous fat, genital fat, and intra-abdominal fat depending on the concentrations as compared with the control group that was administered with sterile distilled water as compared with initial body weight (see FIG. 3 to FIG. 5). In addition, it also had effects on decreasing the total amount of fat (see FIG. 6) and the weight of liver (see FIG. 7).

Accordingly, it could be found that the high water-soluble 2-hydroxypropyl-β-cyclodextrin according to the present invention had effects on suppressing an increase in body weight, decreasing body weight, suppressing appetite, decreasing body fat, and decreasing weight of liver.

In Example 3 of the present invention, in order to confirm an effect on normal mice, a change in body weight and an amount of dietary intake were measured after oral-administering the 2-hydroxypropyl-β-cyclodextrins with various concentrations while giving a high fat diet to the normal mice. As a result, the 2-hydroxypropyl-β-cyclodextrin decreased body weight depending on the concentrations as compared with the control group that was oral-administered with sterile distilled water and had a significant effect on decreasing body weight as compared with initial body weight (see FIG. 8). In addition, it had temporarily an effect on suppressing appetite (see FIG. 9).

Figure 10:
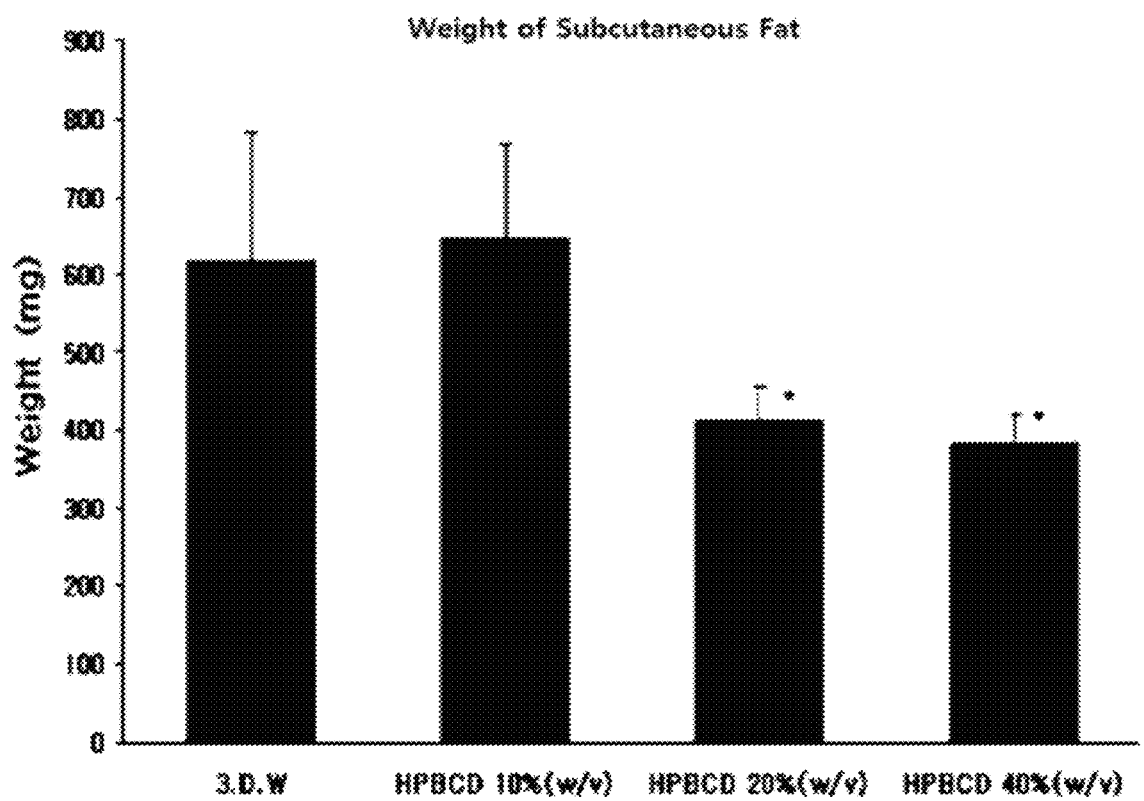
FIG. 10 is a graph showing a change of weight of subcutaneous fat for oral-administering a drinking water including 10%, 20%, and 40% (W/V) of 2-HPBCD in a mouse supplied with a high fat diet.
Figure 11:
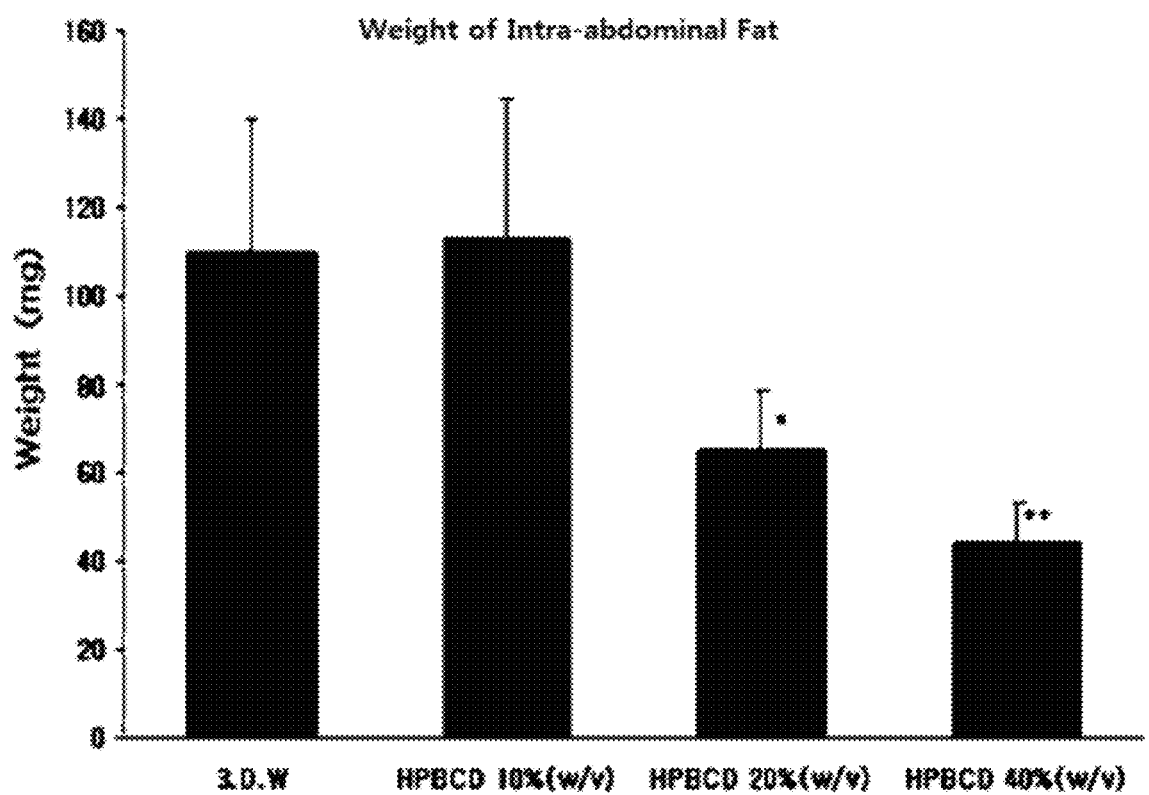
FIG. 11 is a graph showing a change of weight of genital fat for oral-administering a drinking water including 10%, 20%, and 40% (W/V) of 2-HPBCD in a mouse supplied with a high fat diet.
Figure 12:
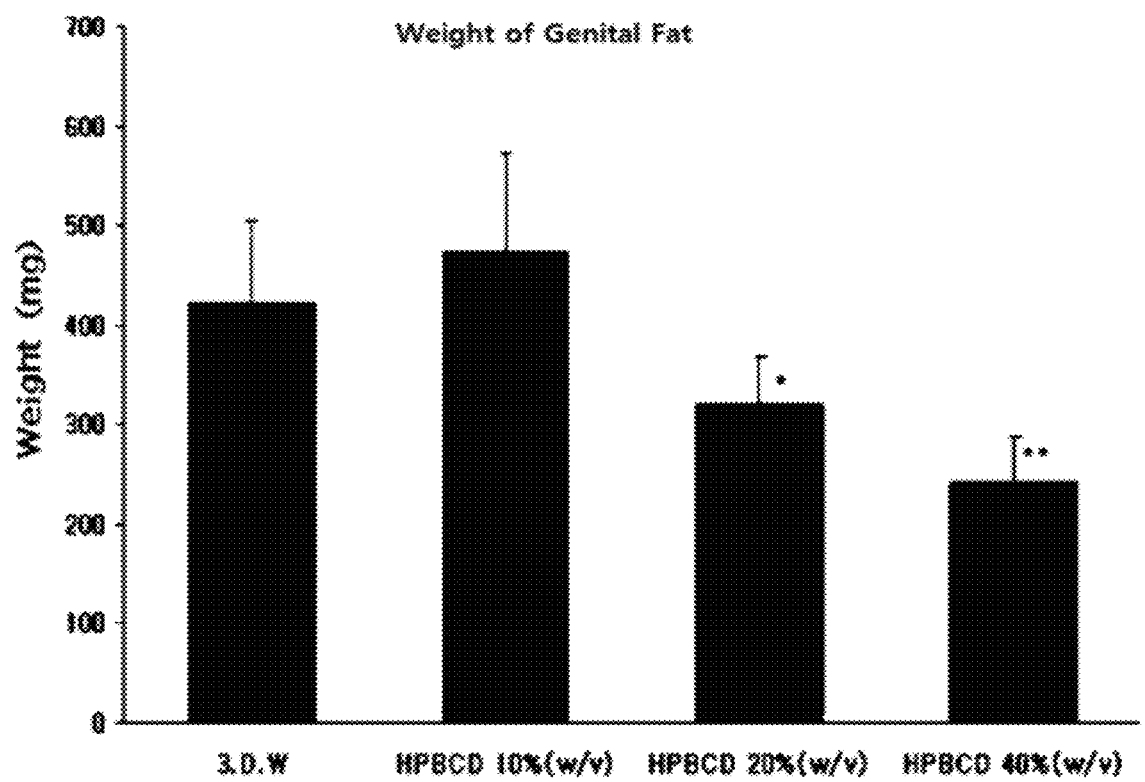
FIG. 12 is a graph showing a change of weight of intra-abdominal fat for oral-administering a drinking water including 10%, 20%, and 40% (W/V) of 2-HPBCD in a mouse supplied with a high fat diet.
Figure 13:
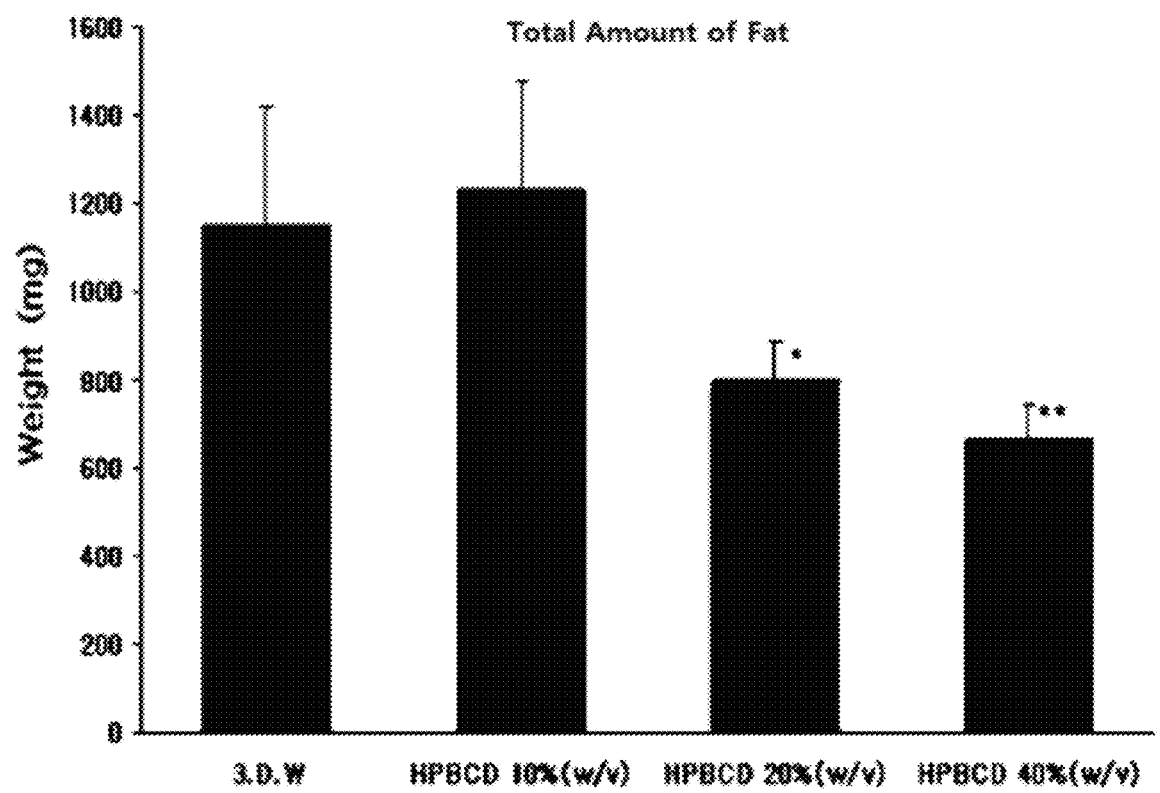
FIG. 13 is a graph showing a change of total weight of fat for oral-administering a drinking water including 10%, 20%, and 40% (W/V) of 2-HPBCD in a mouse supplied with a high fat diet.
Figure 14:
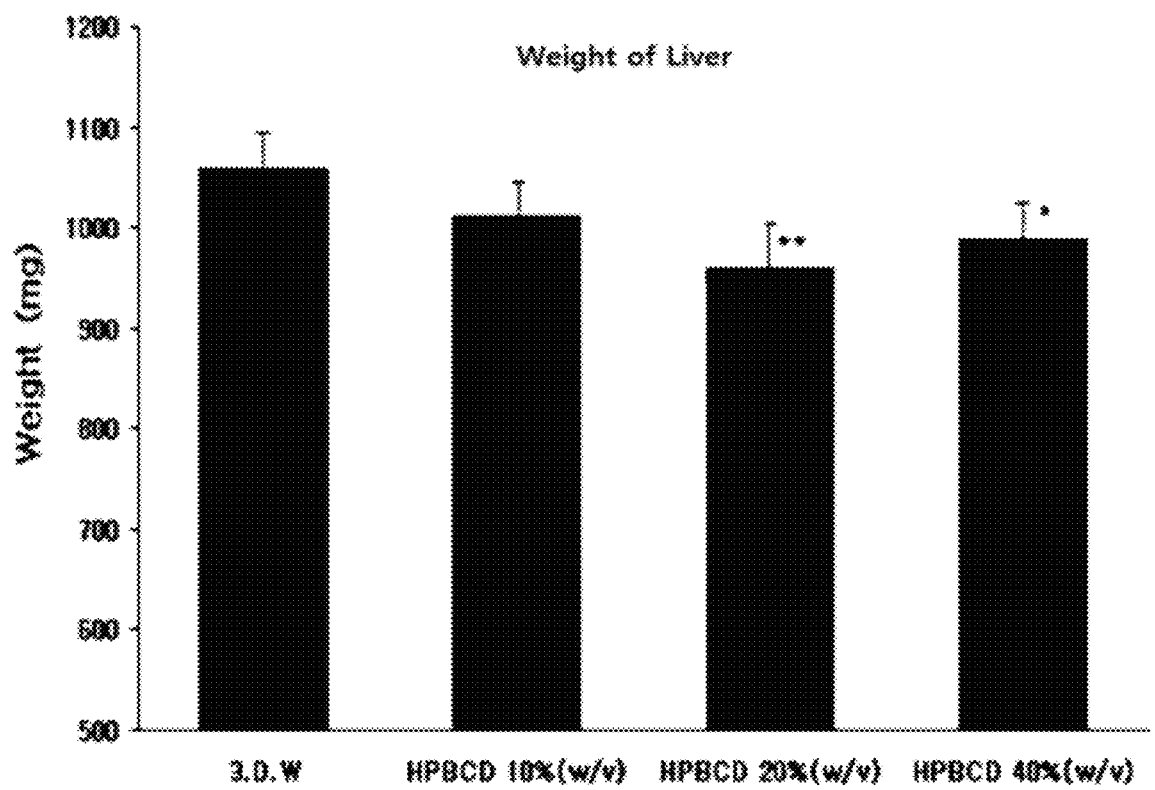
FIG. 14 is a graph showing a change of weight of liver for oral-administering a drinking water including 10%, 20%, and 40% (W/V) of 2-HPBCD in a mouse supplied with a high fat diet.

In Example 4 of the present invention, changes of the weights of subcutaneous fat, genital fat, and intra-abdominal fat, a total amount of fat, and weight of liver were measured, respectively, by autopsying after oral-administering the 2-hydroxypropyl-β-cyclodextrins with various concentrations while giving a high fat diet to normal mice. As a result, the 2-hydroxypropyl-β-cyclodextrin had effects on decreasing the weights of subcutaneous fat, genital fat, and intra-abdominal fat caused by a high fat diet depending on the concentrations as compared with the control group that was oral-administered with sterile distilled water (see FIG. 10 to FIG. 12). In addition, it also had effects on decreasing the total amount of fat (see FIG. 13) and the weight of liver (see FIG. 14).

Accordingly, it could be found that the high water-soluble 2-hydroxypropyl-β-cyclodextrin according to the present invention had effects on suppressing an increase in body weight, decreasing body weight, suppressing appetite, decreasing body fat, and decreasing weight of liver, which were caused by a high fat diet in the mice with normal body weight.

In Example 5 of the present invention, a change in body weight was measured after oral-administering the β-cyclodextrin with various concentrations while giving a high fat diet to normal mice. As a result, the β-cyclodextrin had an effect on suppressing body weight as compared with the control group that was oral-administered with sterile distilled water (see FIG. 15).

Accordingly, it could be found that the β-cyclodextrin decreased an increase in body weight caused by intaking a high fat diet.

In Example 6 of the present invention, in order to confirm whether 2-hydroxypropyl-β-cyclodextrin acts in a similar way as α-cyclodextrin or not, an experiment was performed in a similar way as an experiment for confirming an emulsion forming ability of α-cyclodextrin using a mixture of water and olive oil or corn oil. As a test result, it could be known that the 2-hydroxypropyl-β-cyclodextrin didn't form the emulsion as formed by the α-cyclodextrin in the whole concentration range used for the experiment. From the above fact, it could be known that the 2-hydroxypropyl-β-cyclodextrin had different functional mechanism from that of the α-cyclodextrin.

The β-cyclodextrin derivatives, especially, 2-hydroxypropyl-β-cyclodextrin according to the present invention had a significant high solubility as compared with β-cyclodextrin (Solubility: 2-hydroxypropyl-β-cyclodextrin: >600 mg/mL at 25° C.) so that it can be used in more volume; it can be applied in various dosage forms, and it has high bioavailability.

Accordingly, it could be found that the high water-soluble β-cyclodextrin derivatives, especially, 2-hydroxypropyl-β-cyclodextrin according to the present invention had a significant effect on suppressing an increase in body weight unlike the existing β-cyclodextrin; had a significant high solubility so that it can be plentifully used; and had high bioavailability so that it can be effectively used to suppress body fat and body weight.

In Example of the present invention, in order to compare effects of 2-hydroxypropyl-β-cyclodextrin and β-cyclodextrin on decreasing body weight, a change in body weight was investigated and compared after oral-administering the 2-hydroxypropyl-β-cyclodextrin and β-cyclodextrin with various concentrations, respectively, using animal models suffered from obesity caused by a high fat diet. As a result, it could be found that while the 2-hydroxypropyl-β-cyclodextrin had a significant effect on decreasing body weight to the initial body weight depending on the concentrations as compared with the control group, the β-cyclodextrin had a slight effect on suppressing an increase in body weight, but didn't have an effect on decreasing body weight as compared with the control group (see FIG. 8 to FIG. 15). In addition, while the 2-hydroxypropyl-β-cyclodextrin had a definite effect on decreasing body weight according to the concentrations, β-cyclodextrin had an indefinite effect according to the concentrations. In addition, while it is possible to administer the 2-hydroxypropyl-β-cyclodextrin with 40% (W/V) concentration, it is impossible to administer β-cyclodextrin with 40% (W/V) concentration.

Accordingly, it could be known that the 2-hydroxypropyl-β-cyclodextrin according to the present invention had a superior effect on decreasing body weight to initial body weight as compared with β-cyclodextrin; had high solubility and then high bioavailability as compared with β-cyclodextrin so that a dose-response was definite; and the solubility of β-cyclodextrin was low so that toxicity may be caused after administering.

In addition, the present invention provides a composition for lowering blood sugar, including high water-soluble β-cyclodextrin derivatives as an effective component.

In addition, the present invention provides a composition for suppressing glycolysis in the gastrointestinal tract, including high water-soluble β-cyclodextrin derivatives or a pharmaceutically acceptable salt thereof as an effective component.

In addition, the present invention provides a composition for suppressing absorption of sugar in the gastrointestinal tract, including high water-soluble β-cyclodextrin derivatives or a pharmaceutically acceptable salt thereof as an effective component.

The high water-soluble β-cyclodextrin derivatives may be a type of salt.

Figure 17:
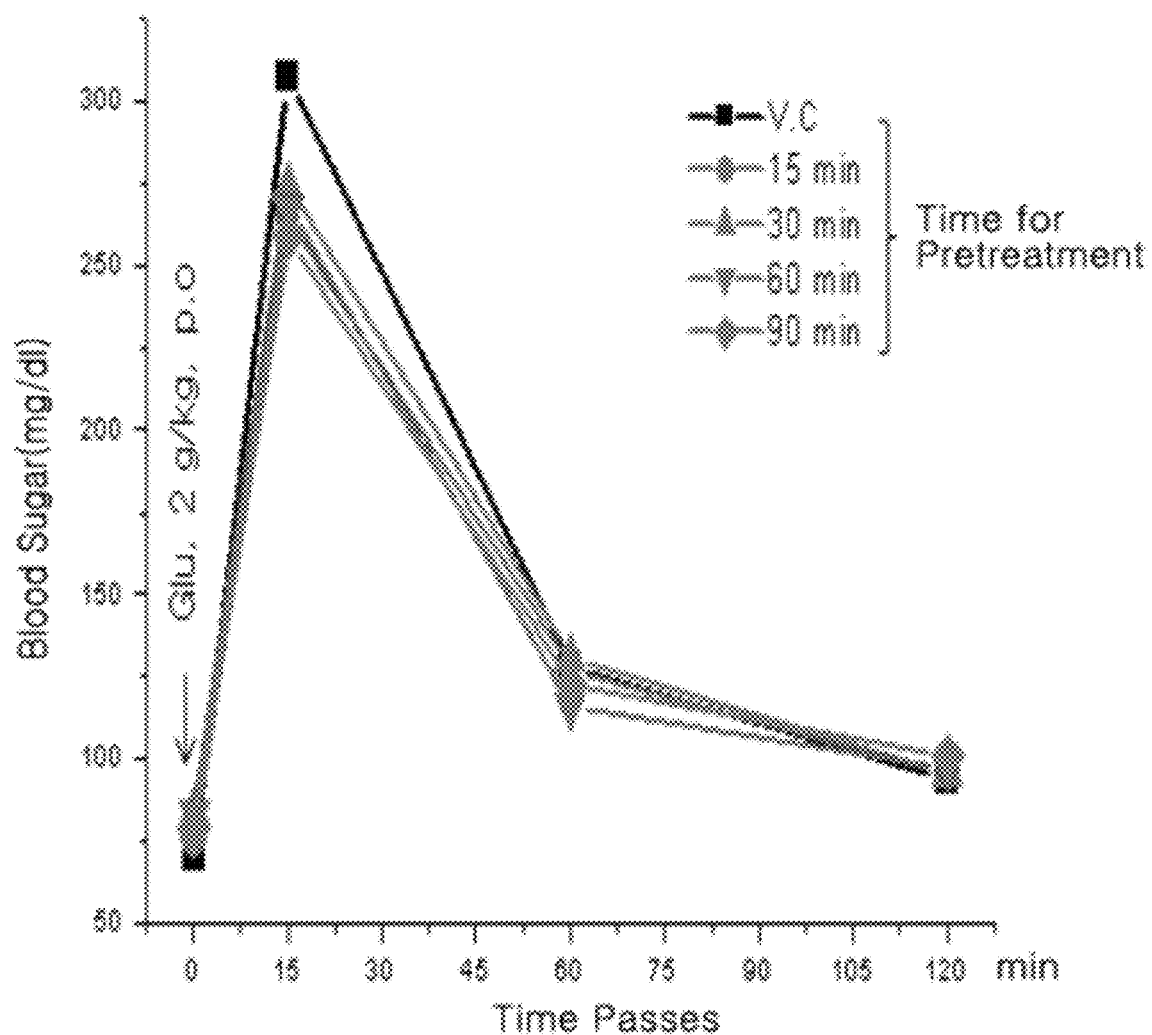
FIG. 17 is a graph showing an effect on suppressing a sharp increase of blood sugar caused by intaking glucose (2 g/kg) on an empty stomach by oral-administering 2-HPBCD with 20% (W/V) concentration before 15 min., 30 min., 60 min., and 90 min., respectively.

In Example 7 of the present invention, in order to confirm whether or not hydroxypropyl-β-cyclodextrin has effects on suppressing a sharp increase of blood sugar caused by intaking glucose and suppressing absorption/decomposition of glucose, the blood sugar was measured after oral-administering glucose following oral-administering the hydroxypropyl-β-cyclodextrin to mice. As a result, it could be found that the blood sugar caused by intaking glucose was suppressed by approximately 19~24% in the group administered with the hydroxypropyl-β-cyclodextrin as compared with the control group (see Table 20 and FIG. 17).

Figure 18:
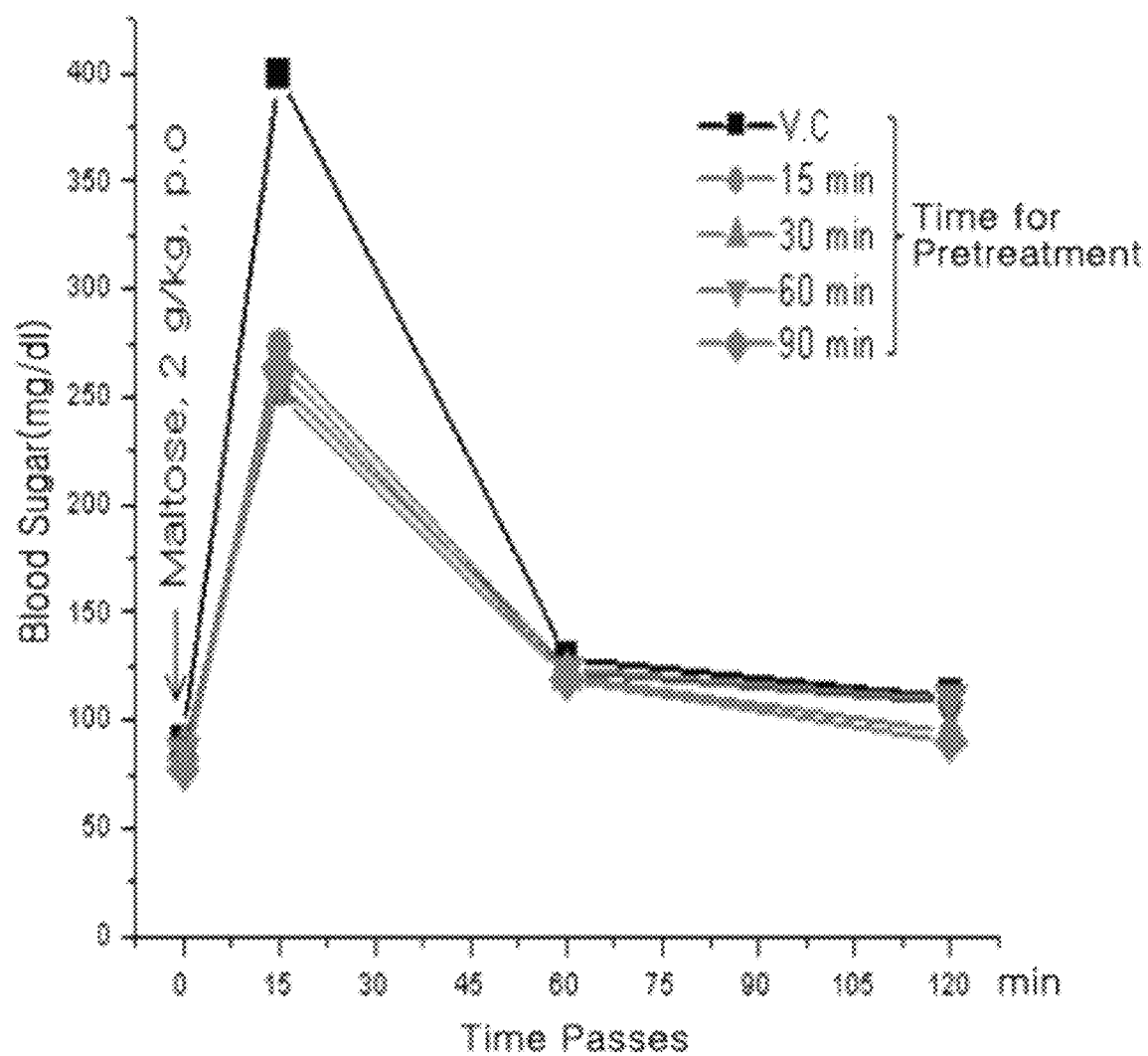
FIG. 18 is a graph showing an effect on suppressing a sharp increase of blood sugar caused by intaking maltose (2 g/kg) on an empty stomach by oral-administering 2-HPBCD with 20% (W/V) concentration before 15 min., 30 min., 60 min., and 90 min., respectively.

In Example 8 of the present invention, in order to confirm whether or not the hydroxypropyl-β-cyclodextrin has an effect on suppressing a sharp increase of blood sugar caused by intaking maltose, the blood sugar was measured after oral-administering maltose following an oral administration of the hydroxypropyl-β-cyclodextrin to mice. As a result, it could be found that the blood sugar caused by intaking maltose was suppressed by approximately 38~47% in the group administered with the hydroxypropyl-β-cyclodextrin as compared with the control group (see Table 21 and FIG. 18).

Accordingly, it has been seen that the high water-soluble β-cyclodextrin derivatives including the hydroxypropyl-β-cyclodextrin may have effects on lowering blood sugar after dinner through an oral-administration and suppressing absorption of sugar in the gastrointestinal tract by suppressing glycolysis.

In conclusion, it has been seen that since the high water-soluble β-cyclodextrin derivatives including the hydroxypropyl-β-cyclodextrin according to the present invention may have a significant effect on suppressing a sharp increase of the blood sugar caused by intaking glucose or maltose on an empty stomach in normal mice, it can be useful to use as an effective component for the composition for suppressing a sharp increase of the blood sugar after dinner.

A composition including the high water-soluble β-cyclodextrin derivatives may further include at least one of an effective component having the same or similar function in addition to the above component.

The composition according to the present invention may further include a pharmaceutically acceptable additive. At this point, the pharmaceutically acceptable additive may include starch, gelatinized starch, microcrystalline cellulose, milk sugar, povidone, colloidal silicon dioxide, calcium hydrogenphosphate, lactose, mannitol, taffy, gum arabic, pregelatinized starch, corn starch, powder cellulose, hydroxypropyl cellulose, opadry, sodium starch glycolate, carnauba wax, synthetic aluminum silicate, stearic acid, magnesium stearate, aluminum stearate, calcium stearate, white sugar, dextrose, sorbitol, talc, etc. The pharmaceutically acceptable additive according to the present invention may preferably be included in 0.1~90 parts by weight based on the above composition, but the present invention is not limited thereto.

The composition of the present invention may be orally or parenterally administered in various dosage forms when actually clinical-administering. A solid medicine for an oral-administration may include tablets, pills, powders, granules, capsules, etc. A liquid medicine for an oral-administration may include suspension, solutions, an emulsion, syrups, etc. A medicine for a parenteral-administration may include a sterilized water solution, a non-aqueous solvent, suspension, an emulsion, and a freeze dried medicine. Preferably, a topical or intraperitoneal injection, an intrarectal injection, a subcutaneous injection, an intravenous injection, an intramuscular injection, or a chest injection may be selected as an injection way when parenterally administering.

A dosage range of the composition according to the present invention may vary according to body weight, age, sex, a body condition, and dietary of patient, the time for an injection, a route for an injection, an excretion rate, severity of disease, etc. The range of the dosage may vary according to body weight, age, sex, a body condition, and dietary of patient, the time for an injection, a route for an injection, an excretion rate, severity of disease, etc; a dosage per day may be 0.00001 to 10 g/kg, and preferably 0.0001 to 1 g/kg based on the amount of β-cyclodextrin derivative; and it may be administered in 1~6 times a day.

The composition of the present invention may be used alone, or used together with an operation, a hormone treatment, a chemical treatment, and the methods using a biological response modifier for preventing and treating obesity.

The present invention provides health functional food for preventing and improving obesity, or the diseases caused by obesity, including high water-soluble β-cyclodextrin derivatives as an effective component.

The diseases caused by obesity may be preferably any one selected from the group consisting of hypertension, hyperlipemia, arteriosclerosis, coronary disease, cerebropathia, and diabetes, but the present invention is not limited thereto.

In addition, the present invention provides health functional food for suppressing an increase in body weight, suppressing appetite, or decreasing body fat, including high water-soluble β-cyclodextrin derivatives or a pharmaceutically acceptable salt thereof as an effective component.

In addition, the present invention provides health functional food for lowering blood sugar, including high water-soluble β-cyclodextrin derivatives as an effective component.

The high water-soluble β-cyclodextrin derivatives may be a type of salt.

For the health functional food of the present invention, the high water-soluble β-cyclodextrin derivatives may be added as it is or may be used along with other foods or components for food, and may be properly used according to the typical methods.

A type of the health functional food is not specifically limited. Example of food that is possible to add with the high water-soluble β-cyclodextrin derivatives may be meat, sausage, bread, chocolate, candies, snacks, confectionery, pizza, Ramen, other noodles, gums, dairy products including ice creams, a sorts of soups, beverages, teas, a health drink, alcohol beverages, vitamin complexes, etc, and may include all of typical health foods.

The composition for a health beverage of the present invention may include various flavoring agents, natural carbohydrates, etc as a supplement component like the typical beverages. The above-mentioned natural carbohydrates may be monosaccharide, such as glucose and fructose, disaccharide, such as maltose and sucrose, and sugar-alcohol, such as dextrin, xylitol, sorbitol, erythritol, etc. A sweetening agent may be a natural sweetening agent, such as thaumatin and stevia extract, a synthetic sweetening agent, such as saccharin and aspartame, etc. A ratio of the natural carbohydrate may be generally approximately 0.01~0.04 g and preferably approximately 0.02~0.03 g per 100 ml of the composition of the present invention.

Beyond that, the health food of the present invention may include various nutritional supplements, vitamins, electrolytes, flavoring agents, colorants, pectic acid and salt thereof, alginic acid and salt thereof, organic acid, protective colloid thickener, pH adjuster, stabilizer, preservative, glycerin, alcohol, carbonating agent used for carbonated beverage, etc. Beyond that, fruit flesh may be included for preparing a natural fruit juices, fruit juices beverages, and vegetable beverages. The above component may be used alone or by mixture. A ratio of the above additives may be generally selected in the range of 0.01~0.1 parts by weight based on 100 parts by weight of the composition of the present invention, but is of little importance.

In addition, the present invention provides a method for preventing or treating obesity, including administering an effective amount of the high water-soluble β-cyclodextrin derivatives to an object.

In addition, the present invention provides a method for suppressing appetite of an object, including administering an effective amount of the high water-soluble β-cyclodextrin derivatives to the object.

In addition, the present invention provides a method for preventing or treating the diseases caused by obesity, including administering an effective amount of the high water-soluble β-cyclodextrin derivatives to an object.

In addition, the present invention provides a method for decreasing body fat of an object, including administering an effective amount of the high water-soluble β-cyclodextrin derivatives to the object.

In addition, the present invention provides a method for lowering blood sugar of an object, including administering an effective amount of the high water-soluble β-cyclodextrin derivatives to the object.

In addition, the present invention provides a method for suppressing glycolysis in the gastrointestinal tract of an object, including administering an effective amount of the high water-soluble β-cyclodextrin derivatives to the object.

In addition, the present invention provides a method for suppressing absorption of sugar in the gastrointestinal tract of an object, including administering an effective amount of the high water-soluble β-cyclodextrin derivatives to the object.

In addition, the present invention provides a use of the high water-soluble β-cyclodextrin derivatives for preparing the composition for preventing or treating obesity.

In addition, the present invention provides a use of the high water-soluble β-cyclodextrin derivatives for preparing the composition for suppressing appetite.

In addition, the present invention provides a use of the high water-soluble β-cyclodextrin derivatives for preparing the composition for preventing or treating the diseases caused by obesity.

In addition, the present invention provides a use of the high water-soluble β-cyclodextrin derivatives for preparing the composition for decreasing body fat.

In addition, the present invention provides a use of the high water-soluble β-cyclodextrin derivatives for preparing the composition for lowering blood sugar.

In addition, the present invention provides a use of the high water-soluble β-cyclodextrin derivatives for preparing the composition for suppressing glycolysis in the gastrointestinal tract.

In addition, the present invention provides a use of the high water-soluble β-cyclodextrin derivatives for preparing the composition for suppressing adsorption of sugar in the gastrointestinal tract.

Hereinafter, the present invention will be described in more detail in accordance with Examples and Preparation examples.

However, the following Examples and Preparation examples are only for specifically illustrating the present invention and the content of the present invention is not limited to the Examples and Preparation examples.

EXAMPLE 1

Measurement of Change in Body Weight and Amount of Dietary Intake by Autonomically Drinking of HPBCD in Mouse Model Suffered from Obesity Caused by High Fat Diet Male C57BL/6J mice (Five age of the week, KRIBB, Korea) were accommodated for 1 week, and then were induced with obesity by giving a high fat diet (60% fat kcal, Research Diets) for 15 days. The weights of the animals that were induced with obesity were equally divided into 3 animals as one group. And then, the solvent-control group drank sterilized distilled water, autonomically. Hydroxypropyl-β-cyclodextrin (HPBCD) was dissolved in sterilized distilled water to be 10, 15, and 20% (W/V) concentrations for drinking autonomically. A change in body weight was daily measured to all of animals during the test; the fixed amount of feeds was provided at the day of measuring body weight, and then an amount of intake per a group (g/day) was calculated by measuring a residual amount of feeds at the next day.

TABLE 1

| | Change in body weight (%) | | | |
|---|---|---|---|---|
| Sample | 0 Day | 1 Day | 2 Day | 3 Day |
| Distilled Water | 100.0 ± 0.0 | 100.2 ± 1.5 | 101.4 ± 1.4 | 101.3 ± 2.0 |
| HPBCD 10% (w/v) | 100.0 ± 0.0 | 98.1 ± 0.2 | 97.6 ± 0.8* | 94.6 ± 0.7** |
| HPBCD 15% (w/v) | 100.0 ± 0.0 | 96.1 ± 1.1* | 94.0 ± 1.3** | 90.9 ± 2.3** |
| HPBCD 20% (w/v) | 100.0 ± 0.0 | 100.0 ± 0.0 | 89.1 ± 6.9* | 85.4 ± 8.1* |

Significant (Students t-test): *p < 0.05, **p < 0.01

TABLE 2

| | Amount of Feed Intake (g/day) | | |
|---|---|---|---|
| Sample | 1 Day | 2 Day | 3 Day |
| Distilled Water | 5.7 | 6.9 | 5.6 |
| HPBCD 10% (w/v) | 3.9 | 3.9 | 2.7 |
| HPBCD 15% (w/v) | 4.1 | 4.5 | 4.0 |
| HPBCD 20% (w/v) | 4.2 | 4.2 | 2.6 |

Figure 2:
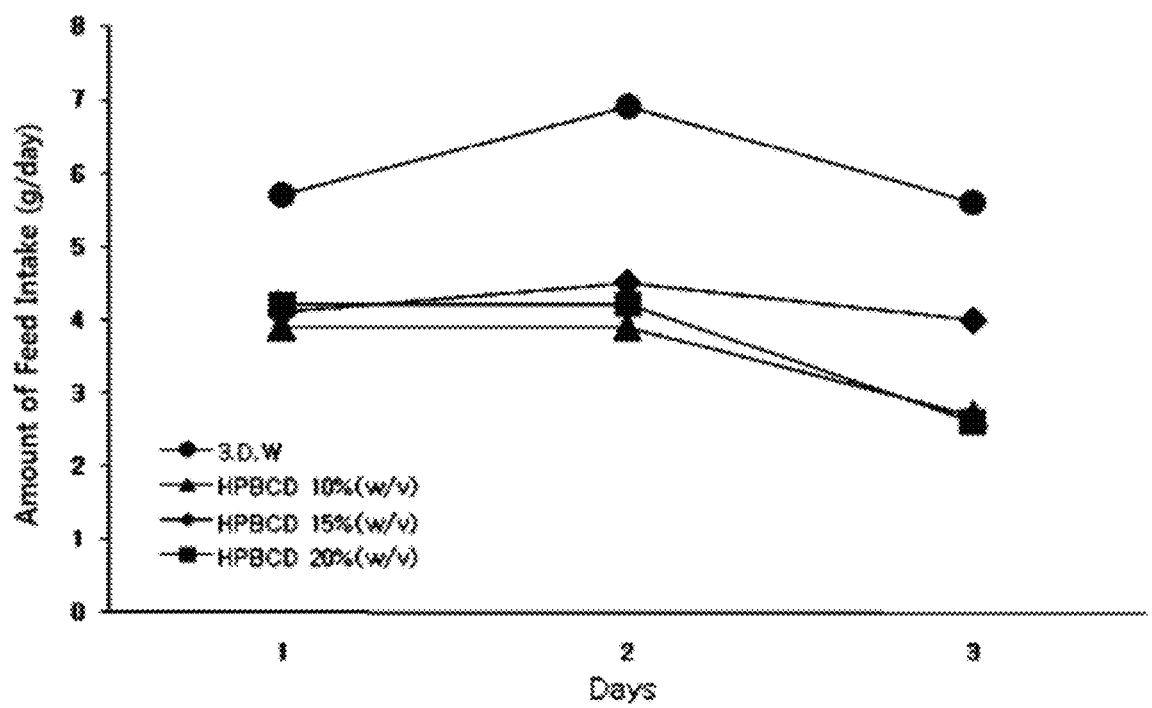
FIG. 2 is a graph showing a change of feed intake for autonomically drinking a drinking water including 10%, 15%, and 20% (W/V) of 2-HPBCD in a mouse model with obesity caused by a high fat diet.

As a result, as shown in Table 1 and FIG. 1, it has been seen that the body weight was decreased depending on the concentration as compared with the autonomically sterilized distilled water-drinking control group when the mice supplied with a high fat diet drank HPBCD with the above concentrations, autonomically, and also the body weight was significantly decreased as compared with the initial body weight (FIG. 1). In addition, as shown in Table 2 and FIG. 2, it has been seen that HPBCD had an effect on suppressing appetite through a decrease of dietary intake (FIG. 2).

EXAMPLE 2

Measurement of Weights of Body Fat and Liver by Autonomically Drinking HPBCD in Mouse Model with Obesity Caused by High Fat Diet The animals induced with obesity in the above <Example 1> drank autonomically HPBCD with 10, 15, and 20% (W/V) concentrations for 3 days and then their autopsies were conducted. The mice were killed by using $CO_2$ gas; their abdomens were cut; their genital fats, intra-abdominal fats, and livers were isolated; then their weights were measured using a chemical balance; average weight of three animals was calculated.

TABLE 3

| Sample | Weight of Subcutaneous Fat (mg) |
|---|---|
| Distilled Water | 898.0 ± 138.1 |
| HPBCD 10% (w/v) | 862.2 ± 86.7 |
| HPBCD 15% (w/v) | 765.1 ± 238.8 |
| HPBCD 20% (w/v) | 489.4 ± 183.5* |

TABLE 4

| Sample | Weight of Intra-abdominal Fat (mg) |
|---|---|
| Distilled Water | 215.3 ± 32.3 |
| HPBCD 10% (w/v) | 158.8 ± 36.3 |
| HPBCD 15% (w/v) | 147.2 ± 29.2 |
| HPBCD 20% (w/v) | 97.8 ± 44.9* |

TABLE 5

| Sample | Weight of Genital Fat (mg) |
| --- | --- |
| Distilled Water | 726.9 ± 123.0 |
| HPBCD 10% (w/v) | 594.0 ± 95.0 |
| HPBCD 15% (w/v) | 524.8 ± 67.1 |
| HPBCD 20% (w/v) | 448.4 ± 108.6* |

TABLE 6

| Sample | Total Amount of Fat (mg) |
| --- | --- |
| Distilled Water | 1840.2 ± 280.1 |
| HPBCD 10% (w/v) | 1615.0 ± 212.3 |
| HPBCD 15% (w/v) | 1437.0 ± 282.0 |
| HPBCD 20% (w/v) | 1035.6 ± 324.3* |

TABLE 7

| Sample | Weight of Liver (mg) |
| --- | --- |
| Distilled Water | 1245.6 ± 235.4 |
| HPBCD 10% (w/v) | 999.3 ± 150.2 |
| HPBCD 15% (w/v) | 820.5 ± 66.0* |
| HPBCD 20% (w/v) | 808.7 ± 76.8* |

Significant (Students t-test): *$p < 0.05$

As a result, as shown in Table 3 to Table 7 and FIG. 3 to FIG. 7, it has been seen that the amounts of subcutaneous fats, genital fats, intra-abdominal fats, and total amount of fats of the mice induced by a high fat diet were decreased and also the weight of liver was decreased depending on the concentrations as compared with the autonomically sterilized distilled water-drinking control group when autonomically drinking HPBCD with the above concentrations (FIG. 3 to FIG. 7).

EXAMPLE 3

Measurement of Amount of Dietary Intake and Change in Body Weight by Oral Administration of BPBCD in High Fat Diet-Mouse Male C57BL/6J mice (Five age of the week, KRIBB, Korea) were accommodated for 1 week. And then, the weights of the animals were equally divided into 5 animals as one group. While a high fat diet (60% fat kcal) was provided, sterilized distilled water and HPBCDs with 10, 20, and 40% (W/V) were orally administered at three times (Morning, Afternoon, Evening) a day for 5 days in 0.2 ml per 20 g body weight of a mouse at the same time. A change in body weight was measured to all of the animals during the test at one time per day; the fixed amount of feeds was provided at the day of measuring body weight, and then an average amount of intake per an animal (g/mouse/day) was calculated by measuring a residual amount of feeds at the next day.

TABLE 8

| | Change in body weight (%) | | | | | |
| --- | --- | --- | --- | --- | --- | --- |
| Sample | 0 Day | 1 Day | 2 Day | 3 Day | 4 Day | 5 Day |
| Distilled Water | 100.0 ± 0.0 | 101.3 ± 1.2 | 101.5 ± 1.6 | 102.2 ± 2.7 | 102.5 ± 3.4 | 103.2 ± 3.9 |
| HPBCD 10% (w/v) | 100.0 ± 0.0 | 99.3 ± 0.9 * | 98.5 ± 1.3 * | 98.4 ± 1.2 * | 98.3 ± 1.2 * | 98.7 ± 2.0 * |
| HPBCD 20% (w/v) | 100.0 ± 0.0 | 97.1 ± 1.0 *** | 95.6 ± 1.1 *** | 95.8 ± 1.3 ** | 96.6 ± 1.0 ** | 95.7 ± 1.5 ** |
| HPBCD 40% (w/v) | 100.0 ± 0.0 | 95.0 ± 2.2 *** | 93.1 ± 3.4 ** | 93.5 ± 3.4 ** | 94.3 ± 2.9 ** | 94.1 ± 1.9 ** |

Significant (Students t-test):
* $p < 0.05$,
** $p < 0.01$,
*** $p < 0.001$

TABLE 9

| | Amount of Feed Intake (g/mouse/day) | | | | |
| --- | --- | --- | --- | --- | --- |
| Sample | 1 Day | 2 Day | 3 Day | 4 Day | 5 Day |
| Distilled Water | 3.1 ± 0.2 | 2.7 ± 0.3 | 2.9 ± 0.3 | 2.5 ± 0.3 | 2.5 ± 0.3 |
| HPBCD 10% (w/v) | 3.0 ± 0.2 | 2.8 ± 0.3 | 2.9 ± 0.5 | 2.7 ± 0.5 | 2.7 ± 0.5 |
| HPBCD 20% (w/v) | 2.4 ± 0.4 | 2.1 ± 0.4 | 2.5 ± 0.4 | 2.6 ± 0.2 | 2.1 ± 0.4 |
| HPBCD 40% (w/v) | 1.8 ± 0.5 | 2.0 ± 0.5 | 2.7 ± 0.6 | 2.5 ± 0.3 | 2.6 ± 0.3 |

Figure 8:
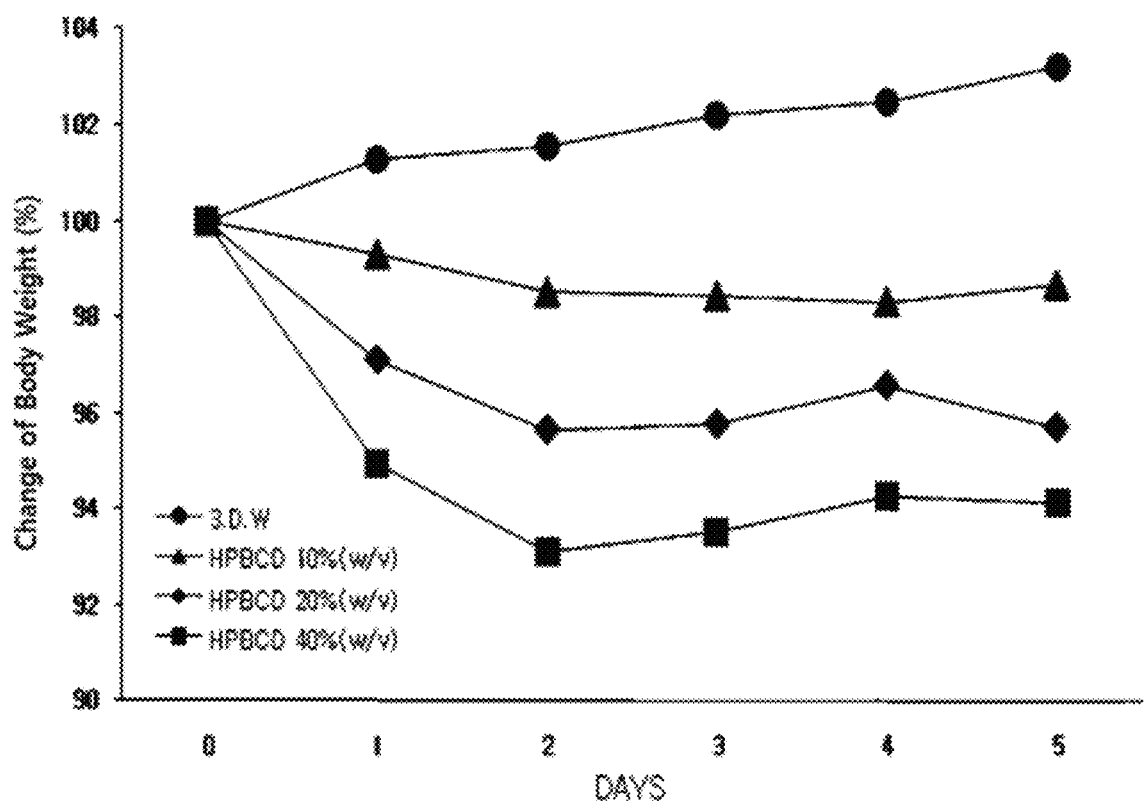
FIG. 8 is a graph showing an effect on decreasing body weight for oral-administering a drinking water including 10%, 20%, and 40% (W/V) of 2-HPBCD in a mouse supplied with a high fat diet.
Figure 9:
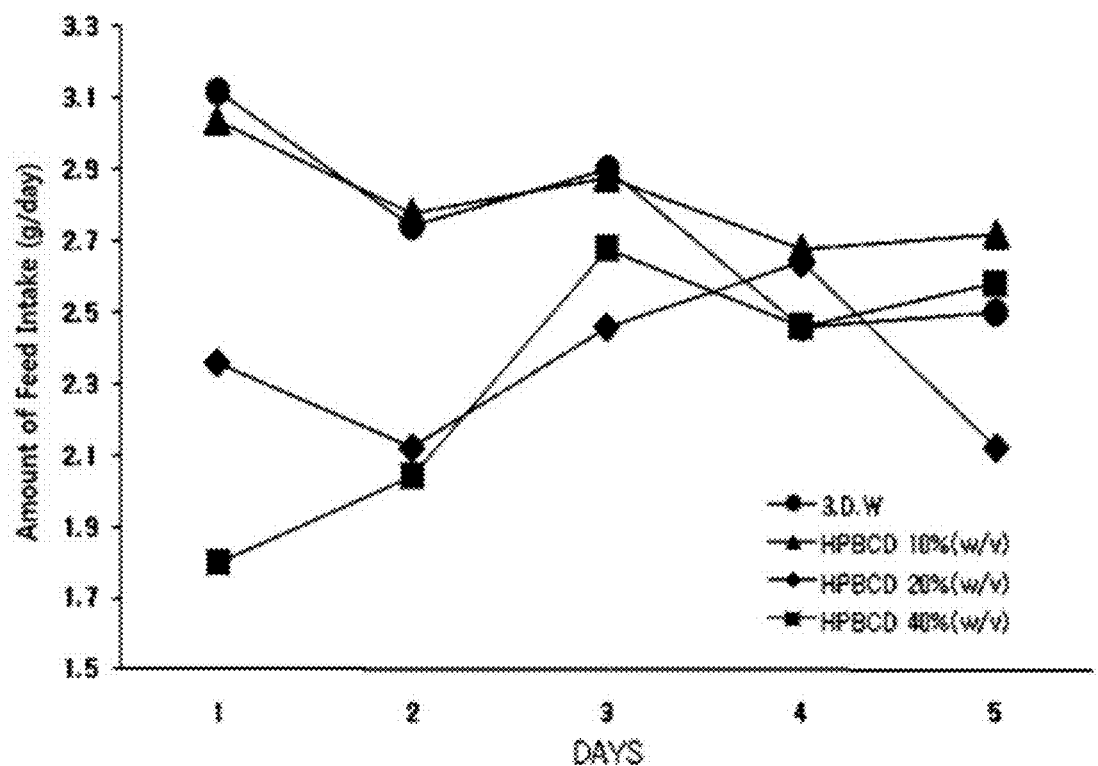
FIG. 9 is a graph showing a change of feed intake for oral-administering a drinking water including 10%, 20%, and 40% (W/V) of 2-HPBCD in a mouse supplied with a high fat diet.

As a result, as shown in Table 8 and FIG. 8, it has been seen that the body weight was decreased depending on the concentrations as compared with the autonomically sterilized distilled water-drinking control group when orally administering HPBCD with the above concentrations in a high fat diet-mouse and also the body weight was significantly decreased as compared with the initial body weight (FIG. 8). In addition, as shown in Table 9 and FIG. 9, it has been seen that HPBCD had a temporary effect on decreasing an amount of dietary intake during the test (FIG. 9).

EXAMPLE 4

Measurement of Change of Liver Weight and Body Fat by Orally Administering HPBCD in High Fat Diet-Mouse Under the administration condition and animal accommodation in the above <Example 3>, HPBCDs with 10, 20, and 40% (W/V) concentrations were orally administered for 5 days and then the mice's autopsies were conducted. The mice were killed by using $CO_2$ gas; their abdomens were cut; their subcutaneous fats, genital fats, intra-abdominal fats, and livers were isolated; then their weights were measured using a chemical balance; average weight of five animals was calculated.

TABLE 10

| Sample | Weight of Subcutaneous Fat (mg) |
|---|---|
| Distilled Water | 618.6 ± 163.6 |
| HPBCD 10% (w/v) | 647.6 ± 119.5 |
| HPBCD 15% (w/v) | 411.3 ± 43.9 * |
| HPBCD 20% (w/v) | 382.1 ± 38.3 * |

TABLE 11

| Sample | Weight of Intra-abdominal Fat (mg) |
|---|---|
| Distilled Water | 110.1 ± 30.1 |
| HPBCD 10% (w/v) | 113.0 ± 31.5 |
| HPBCD 15% (w/v) | 64.9 ± 13.3 * |
| HPBCD 20% (w/v) | 43.9 ± 9.3 ** |

TABLE 12

| Sample | Weight of Genital Fat (mg) |
|---|---|
| Distilled Water | 422.5 ± 84.1 |
| HPBCD 10% (w/v) | 473.3 ± 99.6 |
| HPBCD 15% (w/v) | 319.6 ± 46.5 * |
| HPBCD 20% (w/v) | 240.8 ± 45.5 ** |

TABLE 13

| Sample | Total Amount of Fat (mg) |
|---|---|
| Distilled Water | 1151.1 ± 267.6 |
| HPBCD 10% (w/v) | 1233.9 ± 244.8 |
| HPBCD 15% (w/v) | 795.8 ± 90.1 * |
| HPBCD 20% (w/v) | 666.9 ± 75.3 ** |

TABLE 14

| Sample | Weight of Liver (mg) |
|---|---|
| Distilled Water | 1058.3 ± 36.8 |
| HPBCD 10% (w/v) | 1011.1 ± 33.5 |
| HPBCD 15% (w/v) | 960.2 ± 44.6 ** |
| HPBCD 20% (w/v) | 990.1 ± 35.1 * |

Significant (Students t-test): * $p < 0.05$, ** $p < 0.01$

As a result, as shown in Table 10 to Table 14 and FIG. 10 to FIG. 14, it has been seen that the weights of subcutaneous fats, genital fats, intra-abdominal fats, and total fats of the mice induced by a high fat diet were decreased and also the weight of liver was decreased depending on the concentrations as compared with the autonomically sterilized distilled water-drinking control group when HPBCDs with the above concentrations were orally administered (FIG. 10 to FIG. 14).

EXAMPLE 5

Measurement of Change in Body Weight by Orally Administering BCD in High Fat Diet-Mouse A body weight was measured by using the same conditions as the above <Example 3>, except that BCDs with 10 and 20% (W/V) concentrations were used instead of HPBCDs with 10, 20, and 40% (W/V) concentrations. Since the solubility of BCD is >600 mg/mL, the solution with 40% (W/V) was not prepared so that only BCDs with 10 and 20% (W/V) were used for the test.

TABLE 15

| | Change in body weight (%) | | | | | |
|---|---|---|---|---|---|---|
| Sample | 0 Day | 1 Day | 2 Day | 3 Day | 4 Day | 5 Day |
| Distilled Water | 100.0 ± 0.0 | 104.1 ± 1.7 | 104.5 ± 0.5 | 106.4 ± 1.9 | 107.8 ± 1.6 | 109.2 ± 2.0 |
| BCD 10% (w/v) | 100.0 ± 0.0 | 101.5 ± 2.1 | 100.7 ± 1.9 ** | 102.0 ± 2.5 * | 102.4 ± 4.0 * | 103.4 ± 4.1 * |
| BCD 20% (w/v) | 100.0 ± 0.0 | 100.3 ± 2.7 * | 102.1 ± 2.1 * | 103.1 ± 2.1 * | 103.7 ± 3.0 * | 103.2 ± 2.6 ** |

Significant (Students t-test):
* $p < 0.05$,
** $p < 0.01$

Figure 15:
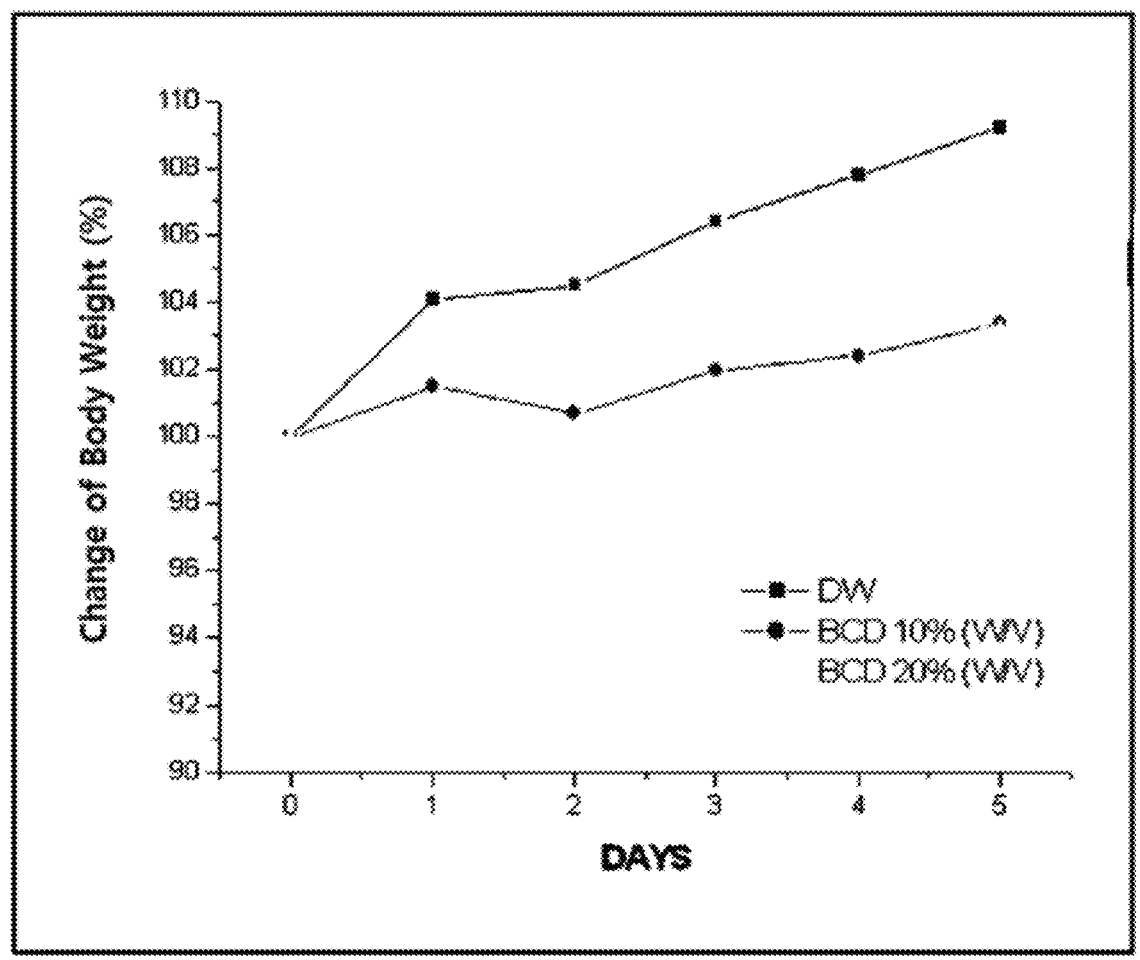
FIG. 15 is a graph showing an effect on suppressing an increase in body weight for oral-administering a drinking water including 10% and 20% (W/V) of β-cyclodextrin (BCD) in a mouse supplied with a high fat diet.

As a result, as shown in Table 15 and FIG. 15, it has been seen that the increase in body weight was suppressed as compared with the sterilized distilled water-oral-administering group when orally administering BCDs with the above concentrations in a high fat diet mouse, but the body weight was not decreased as compared with the initial body weight (FIG. 15). In addition, there was no significant difference between 10 and 20% (W/V) because the bioavailability was low due to a low solubility of BCD so that there was no difference of effects according to the volume.

EXAMPLE 6

Comparative Experiment Between Functional Mechanisms of HPBCD According to Present Invention and Alpha-Cyclodextrin In order to confirm whether or not 2-hydroxypropyl-β-cyclodextrin acts in a similar way to α-cyclodextrin, an emulsion-forming ability was confirmed by using a mixture of water and olive oil or corn oil.

Firstly, HPBCD was added to the solution mixed with 6 ml of water and 4 ml of olive oil or corn oil in the ratios of 0, 1.25, 2.5, 5, 10, 20% (w/v); mixed well; and then centrifuged (at 80×g for 2 minutes). And then, a blue water-soluble dye (trypan blue, Sigma Co.) was added to clearly separate between layers.

Figure 16:
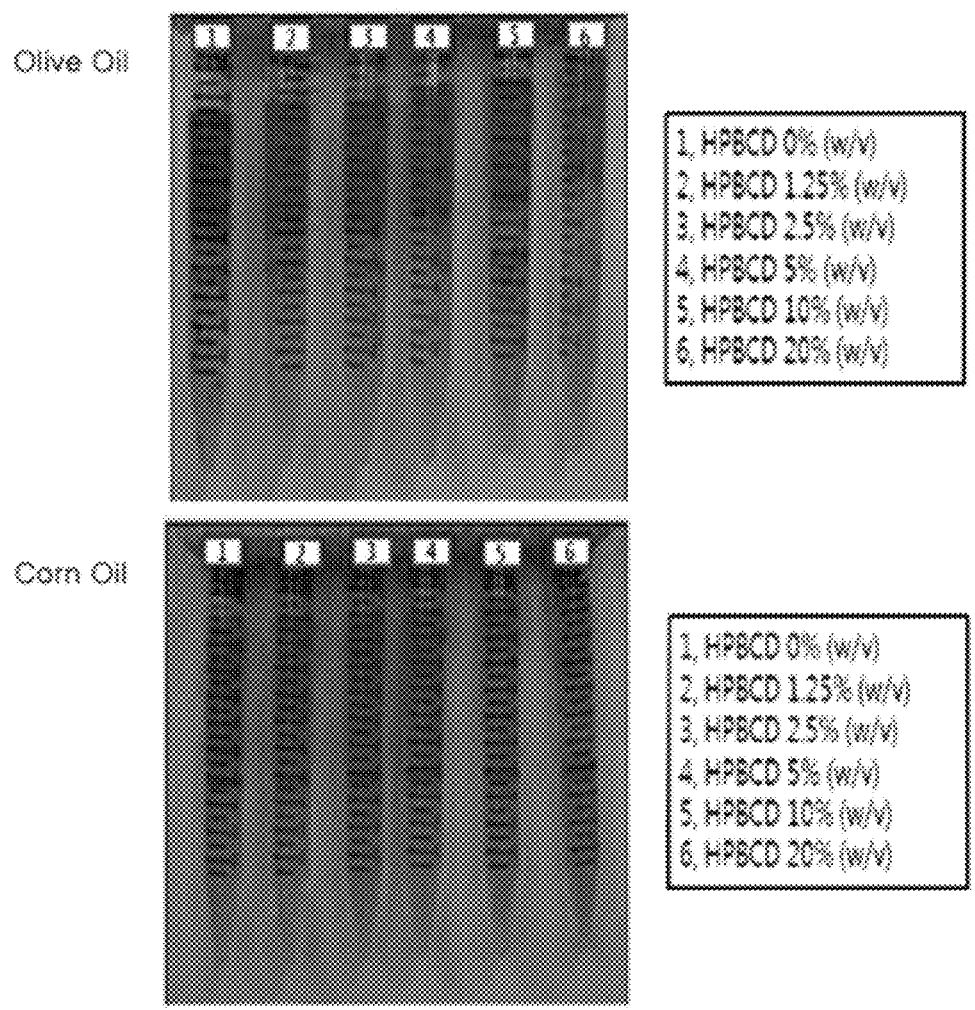
FIG. 16 is a diagram showing effects of 2-HPBCD with various concentrations on a type of the mixture of water and fat.

As a result, as shown in FIG. 16, HPBCD did not form an emulsion at any concentrations used for the test. For reference, it reported in the similar test by using α-cyclodextrin (Grunberger G., et al., *Diabetes Metab. Res. Rev.* 23, pp 56-62, 2007) that α-cyclodextrin was mixed with the mixture solution of water and fat and then stirred to form an emulsion. Accordingly, it has been seen that the 2-hydroxypropyl-β-cyclodextrin has different functional mechanism from the α-cyclodextrin.

COMPARATIVE EXAMPLE 1

<1-1> Measurement of Change in Body Weight by Autonomically Drinking Alpha-Cyclodextrin in Obesity-Induced Mouse Model by High Fat Diet A change in body weight was measured during the test using α-cyclodextrin (α-CD) instead of 2-hydroxypropyl-β-cyclodextrin (HPBCD) in the same method as the above <Example 1>.

TABLE 16

| Sample | Change in body weight (%) | | | |
|---|---|---|---|---|
| | 0 Day | 1 Day | 2 Day | 3 Day |
| α-CD 10% (w/v) | 100.0 ± 0.0 | 100.2 ± 0.2 | 100.6 ± 0.4 | 100.1 ± 1.4 |
| α-CD 15% (w/v) | 100.0 ± 0.0 | 99.8 ± 0.4 | 99.3 ± 0.8 | 98.9 ± 1.1 |
| α-CD 20% (w/v) | 100.0 ± 0.0 | 99.8 ± 0.8 | 99.0 ± 1.4 | 98.5 ± 1.3 |

As a result, as shown in Table 16, the degree of body weight decrease was low when autonomically drinking α-CD by a high fat diet-mouse as compared with HPBCD.

<1-2> Measurement of Change in Body Weight by Orally Administering Alpha-Cyclodextrin in High Fat Diet-Mouse A change in body weight was measured during the test using α-CD instead of HPBCD in the same method as the above <Example 3>.

TABLE 17

| Sample | Change in body weight (%) | | | |
|---|---|---|---|---|
| | 0 Day | 1 Day | 2 Day | 3 Day |
| α-CD 10% (w/v) | 100.0 ± 0.0 | 101.3 ± 0.4 | 100.5 ± 1.6 | 100.2 ± 2.7 |
| α-CD 20% (w/v) | 100.0 ± 0.0 | 99.8 ± 0.8 | 99.5 ± 1.2 | 99.2 ± 1.0 |
| α-CD 40% (w/v) | 100.0 ± 0.0 | 99.6 ± 1.0 | 99.0 ± 1.2 | 98.2 ± 1.3 |

As a result, as shown in Table 17, the degree of body weight decrease was low when autonomically drinking α-CD by a high fat diet-mouse as compared with HPBCD.

COMPARATIVE EXAMPLE 2

<2-1> Measurement of Change in Body Weight by Autonomically Drinking β-Cyclodextrin in Obesity-Induced Mouse Model by High Fat Diet A change in body weight was measured during the test using β-cyclodextrin (β-CD) instead of HPBCD in the same method as the above <Example 1>.

TABLE 18

| Sample | Change in body weight (%) | | | |
|---|---|---|---|---|
| | 0 Day | 1 Day | 2 Day | 3 Day |
| β-CD 10% (w/v) | 100.0 ± 0.0 | 99.8 ± 0.8 | 98.5 ± 1.3 | 98.2 ± 1.2 |
| β-CD 20% (w/v) | 100.0 ± 0.0 | 99.1 ± 1.2 | 98.6 ± 1.2 | 97.5 ± 1.0 |
| β-CD 40% (w/v) | 100.0 ± 0.0 | 98.8 ± 1.1 | 97.0 ± 0.8 | 96.4 ± 1.3 |

As a result, as shown in Table 18, the degree of body weight decrease was low when autonomically drinking β-CD by a high fat diet-mouse as compared with HPBCD.

<2-2> Measurement of Change in Body Weight by Orally Administering β-cyclodextrin in High Fat Diet-Mouse A change in body weight was measured during the test using β-cyclodextrin (β-CD) instead of HPBCD in the same method as the above <Example 3>.

TABLE 19

| Sample | Change in body weight (%) | | | |
|---|---|---|---|---|
| | 0 Day | 1 Day | 2 Day | 3 Day |
| β-CD 10% (w/v) | 100.0 ± 0.0 | 100.5 ± 0.8 | 100.1 ± 1.3 | 99.8 ± 1.2 |
| β-CD 15% (w/v) | 100.0 ± 0.0 | 99.6 ± 1.2 | 99.0 ± 1.4 | 98.5 ± 1.0 |
| β-CD 20% (w/v) | 100.0 ± 0.0 | 99.5 ± 1.1 | 98.6 ± 0.8 | 97.8 ± 1.3 |

As a result, as shown in Table 19, the degree of body weight decrease was low when autonomically drinking β-CD by a high fat diet-mouse as compared with HPBCD.

EXAMPLE 7

Measurement of Effect of HPBCD on Lowering Blood Sugar in Oral Glucose Tolerance Test An oral glucose tolerance test system is to comprehensively predict whether or not a sample has an effect on suppressing a sharp increase of blood sugar induced by intaking glucose after an oral-administration of the sample to a mouse, activities of suppressing glycolysis/glucose absorption, etc.

A normal mouse [ICR, 6W, Coretech Inc., Korea] was accommodated for 1 week, and then approximately 18~20 g female with 7 age of the week mouse was used. 6 mice were assigned for one experimental group and starved for 16 hours to use. Hydroxypropyl-β-cyclodextrin (HPBCD) was dissolved in sterilized distilled water to be 20% (W/V) concentration, and then oral-administered in 0.2 mL per 20 g body weight of a mouse. And then, the glucose dissolved in physiological saline was oral-administered to mice in a liquid amount of 10 ml/kg to inject 2 g/kg after 15, 30, 60, and 90 minutes, respectively. The levels of blood sugars were measured just before administering glucose (0 hour), and at 15, 60, and 120 minutes after administering glucose. Blood for measuring blood sugar was collected from orbital venous of the mouse using a capillary tube. The blood sugar in the collected blood was measured using a measuring instrument, ACCUTREND ALPHA (Boehringer mannheim Co.). The same amount of sterilized distilled water was administered for the control group.

As a result, for all of the experimental groups, when administering D-glucose, the levels of blood sugars were increased, were the highest levels approximately after 15 minutes, and then decreased to be normal levels after 120 minutes. From the result approximately after 15 minuses exhibiting the highest level of blood sugar, it has been seen that the level of blood sugar was increased by 236.7 mg/dl as compared with the level of blood sugar before administering glucose in the case of the control group, but the levels of blood sugars were suppressed by 19.7%, 19.3%, 22.0%, and 23.7%, respectively in the cases of the groups that were pre-treated with HPBCD with 20% (W/V) concentration for 15, 30, 60, and 90 minutes as compared with the control groups. Accordingly, it has been seen that HPBCD had an effect on lowering blood sugar after dinner by orally administering because HPBCD suppressed glycolysis and then sugar absorption (Table 20 and FIG. 17).

EXAMPLE 8

Measurement of Effect of HPBCD on Lowering Blood Sugar in Oral Maltose Tolerance Test An oral maltose tolerance test system is to predict whether or not a sample has an effect on suppressing a sharp increase of blood sugar induced by intaking maltose after an oral-administration of the sample to a mouse.

A normal mouse [ICR, 6W, Coretech Inc., Korea] was accommodated for 1 week, and then approximately 18~20 g female with 7 age of the week mouse was used. 6 mice were assigned for one experimental group and starved for 16 hours to use. HPBCD was dissolved in sterilized distilled water to be 20% (W/V) concentration, and then oral-administered in 0.2 mL per 20 g body weight of a mouse. And then, the maltose dissolved in physiological saline was oral-administered to mice in a liquid amount of 10 ml/kg to inject 2 g/kg after 15, 30, 60, and 90 minutes, respectively. The levels of blood sugars were measured just before administering maltose (0 hour), and at 15, 60, and 120 minutes after administering maltose. Blood for measuring blood sugar was collected from orbital venous of the mouse using a capillary tube. The blood sugar in the collected blood was measured using a measuring instrument, ACCUTREND ALPHA (Boehringer mannheim Co.). The same amount of sterilized distilled water was administered for the control group.

As a result, for all of the experimental groups, when administering maltose, the levels of blood sugars were increased, were the highest levels approximately after 15 minutes, and then decreased to be normal levels after 120 minutes. From the result approximately after 15 minuses exhibiting the highest level of blood sugar, it has been seen that the level of blood sugar was increased by 309.0 mg/dl as compared with the level of blood sugar before administering maltose in the case of the control group, but the levels of blood sugars were suppressed by 38.6% ($p<0.001$), 46.7% ($p<0.001$), 44.6% ($p<0.001$), and 39.6% ($p<0.001$), respectively in the cases of the groups that were pre-treated with HPBCD with 20% (W/V) concentration for 15, 30, 60, and 90 minutes as compared with the control groups. Accordingly, it has been seen that HPBCD had an effect on lowering blood sugar after dinner by orally administering (Table 21 and FIG. 18).

TABLE 20

Effect on Lowering Blood Sugar by Orally Administering HPBCD in Oral Glucose Tolerance Test System

| | | 0 Hour | Level of Blood Sugar Before and After Administration of D-glucose (mg/dl) 15 min. | Increasing Amount of Blood Sugar (15 min.~0 hour) | Rate of Suppression (%)[a] |
|---|---|---|---|---|---|
| Control Group (Sterilized Distilled Water) | | 70.8 | 307.5 | 236.7 | |
| HPBCD 20% (W/V) | (−)15 min. | 74.8 | 264.8 | 190.0 | 19.7 |
| | (−)30 min. | 83.3 | 274.3 | 191.0 | 19.3 |
| | (−)60 min. | 83.3 | 267.8 | 184.5 | 22.0 |
| | (−)90 min. | 78.3 | 259.0 | 180.7 | 23.7 |

[a]Rate of Suppression (%) = [(Sample-treating group/Solvent-treating group) Increasing Amount of Blood Sugar × 100] − 100

TABLE 21

Effect on Lowering Blood Sugar by Orally Administering HPBCD in Oral Maltose Tolerance Test System

|  |  | Level of Blood Sugar Before and After Administration of Maltose (mg/dl) | | Increasing Amount of Blood Sugar (15 min.~0 hour) | Rate of Suppression (%)[a] |
|---|---|---|---|---|---|
|  |  | 0 hour | 15 min. |  |  |
| Control Group (Sterilized Distilled Water) |  | 90.2 | 399.2 | 309.0 |  |
| HPBCD 20% (W/V) | (−)15 min. | 83.2 | 272.8 | 189.7 | 38.6 |
|  | (−)30 min. | 87.2 | 252.0 | 164.8 | 46.7 |
|  | (−)60 min. | 86.2 | 257.5 | 171.3 | 44.6 |
|  | (−)90 min. | 77.7 | 264.2 | 186.2 | 39.6 |

[a]Rate of Suppression (%) = [(Sample-treating group/Solvent-treating group) Increasing Amount of Blood Sugar × 100] − 100

Hereinafter, Preparation examples for preparing the composition of the present invention will be illustrated.

PREPARATION EXAMPLE 1

Preparation of Pharmaceutical Medicine

<1-1> Preparation of Power

| HPBCD | 200 mg |
|---|---|
| Milk sugar | 20 mg |

After mixing the above components, the mixture was filled in an airtight container to prepare powder.

<1-2> Preparation of Tablet

| HPBCD | 500 mg |
|---|---|
| Corn starch | 100 mg |
| Milk sugar | 100 mg |
| Magnesium Stearate | 2 mg |

After mixing the above components, the mixture was compressed according to a typical method for preparing tablets to prepare tablets.

<1-3> Preparation of Capsules

| HPBCD | 500 mg |
|---|---|
| Crystalline cellulose | 3 mg |
| Lactose | 14.8 mg |
| Magnesium Stearate | 0.2 mg |

After mixing the above components, the mixture was filled to a gelatin capsule according to a typical method for preparing capsules to prepare capsules.

<1-4> Preparation of Liquid Medicine

| HPBCD | 2 g |
|---|---|
| Isomerized glucose syrup | 10 g |
| Mannitol | 5 g |
| Purified water | Suitable amount |

Each component was dissolved in purified water according to a typical method for preparing a liquid medicine; a suitable amount of lemon flavoring was added; each of the above components was mixed; purified water was added to the mixture to be total 100 ml; and then the mixture was filled in a brown bottle and sterilized to prepare a liquid medicine.

<1-6> Preparation of Injections

| HPBCD | 10 mg/ml |
|---|---|
| Dilute hydrochloric acid BP | Until pH 7.6 |
| Popular Sodium chloride BP | Maximum 1 ml |

HPBCD was dissolved in a popular sodium chloride BP of a proper volume, the resulted solution was adjusted to be pH 7.6 with a dilute hydrochloric acid BP, the volume was adjusted with the popular sodium chloride BP, and then fully mixed. The resulted solution was filled in an ampoule of 5 ml Type I manufactured with a transparent glass, it was sealed under a top lattice of air by dissolving the glass, it was autoclaved at 120° C. for at least 15 minutes for sterilization to prepare the injections.

PREPARATION EXAMPLE 2

Preparation of Food

The foods including HPBCD of the present invention were prepared as follows.

<2-1> Preparation of Natural Food

Brown rice, barley, glutinous rice, and adlay were pregelatinzed using the known method; dried; roasted; and then powderized with a grinder to prepare a powder with grain-size 60 mesh.

Black bean, black sesame, and perilla seeds were steamed with the known method; dried; roasted; and then powderized by using a grinder to prepare a powder with grain-size 60 mesh.

HPBCD of the present invention was pressure-concentrated in a vacuum condenser; sprayed; dried with a hot-air dryer to obtain a dry matter. Then, the dry matter was ground with a grinder to prepare a dry powder with grain-size 60 mesh.

The grains, seeds, and HPBCD that were prepared as mentioned above were mixed as the following ratio to prepare.

Grains (30 parts by weight of brown rice, 15 parts by weight of adlay, 20 parts by weight of barley), Seeds (7 parts by weight of perilla seeds, 8 parts by weight of black bean, 7 parts by weight of black sesame)
HPBCD (12 parts by weight),
Lacquer top (0.5 parts by weight),
Foxglove (0.5 parts by weight)

<2-2> Preparation of Health Food

| HPBCD | 10 g |
|---|---|
| Vitamins Mixture | Suitable amount |
| Vitamin A acetate | 70 ug |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 ug |
| Vitamin C | 10 mg |
| Biotin | 10 ug |
| Nicotinamide | 1.7 mg |
| Folate | 50 ug |
| Calcium pantothenate | 0.5 mg |
| Minerals mixture | Suitable amount |
| Ferrous sulfate | 1.75 mg |
| Zinc oxide | 0.82 mg |
| Magnesium carbonate | 25.3 mg |
| Potassium Phosphate Monobasic | 15 mg |
| Potassium Phosphate dibasic | 55 mg |
| Potassium citrate | 90 mg |
| Calcium carbonate | 100 mg |
| Magnesium chloride | 24.8 mg |

As the component ratios of the above vitamins and minerals mixtures, the components relatively suitable for health foods may be mixed according to a preferable Example, but the mixing ratio may be modified; the above components may be mixed according to a general method for preparing health foods to prepare granules; and may be used for preparing the composition of health food according to a general method.

PREPARATION EXAMPLE 3

Preparation of Health Food

| HPBCD | 10 g |
|---|---|
| Citric Acid | 100 mg |
| Oligosaccharide | 100 mg |
| Plum Concentrate | 2 mg |
| Taurine | 100 mg |
| Total volume by adding purified water | 500 ml |

After mixing the above components according to a typical method for preparing health beverage, the mixture was stirred and heated at 80° C. for approximately 1 hour; the resulted solution was filtered; filled in a sterilized 1 l container; sealed; sterilized; and then refrigerated to use for preparing the composition of health beverage according to the present invention.

As the component ratio, relatively suitable components for a favorite beverage were mixed according to a preferable Example, but the ratio can optionally be modified and used according to regional and national preferences, such as a demand class, a demand country, a usage, etc.

As set forth above, according to exemplary embodiments of the invention, High water-soluble β-cyclodextrin derivatives, especially, 2-Hydroxypropyl-β-cyclodextrin (HPBCD) according to the present invention has significant effects on suppressing an increase in body weight, suppressing appetite, decreasing body fat, decreasing liver weight, suppressing a sharp increase of blood sugar caused by intaking glucose and maltose on an empty stomach so that it can be useful for preventing and treating obesity, preventing and treating diseases caused by obesity, and suppressing a sharp increase of blood sugar after dinner.

As shown in the above sentences, the present invention provides a drug for preventing and treating obesity or the diseases caused by obesity, using high water-soluble β-cyclodextrin derivatives, especially, 2-hydroxypropyl-β-cyclodextrin, a pharmaceutically acceptable composition for suppressing a sharp increase of blood sugar after dinner, and health functional foods thereof.

While the present invention has been shown and described in connection with the exemplary embodiments, it will be apparent to those skilled in the art that modifications and variations can be made without departing from the spirit and scope of the invention as defined by the appended claims.

What is claimed is:

1. A method for treating obesity, the method comprising orally administering to a subject a composition consisting essentially of 2-hydroxypropyl beta-cyclodextrin having the following Chemical Formula 1 structure:

[Chemical Formula 1]

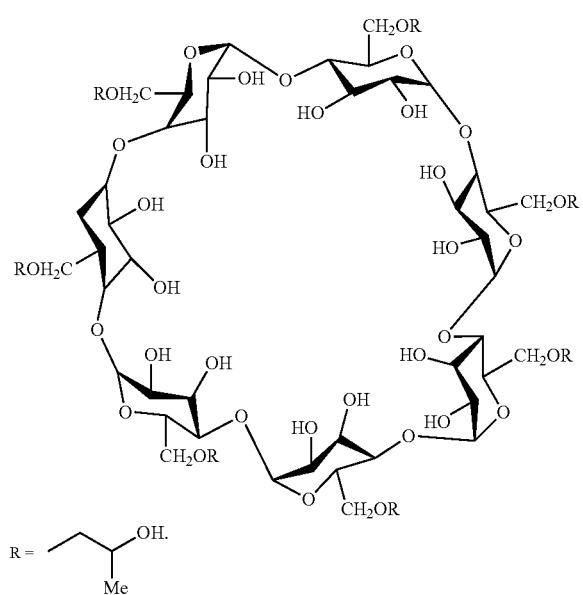

2. The method of claim 1, wherein the therapeutically effective amount of 2-hydroxypropyl beta-cyclodextrin in the composition is in a range from 20% (w/v) concentration to 40% (w/v) concentration.

* * * * *